(12) United States Patent
Maris et al.

(10) Patent No.: US 8,302,480 B2
(45) Date of Patent: Nov. 6, 2012

(54) ENHANCED ULTRA-HIGH RESOLUTION ACOUSTIC MICROSCOPE

(75) Inventors: Humphrey J. Maris, Barrington, RI (US); Arto V. Nurmikko, Providence, RI (US)

(73) Assignee: Brown University, Providence, RI (US)

(*) Notice: Subject to any disclaimer, the term of this patent is extended or adjusted under 35 U.S.C. 154(b) by 1 day.

(21) Appl. No.: 12/449,415

(22) PCT Filed: Feb. 5, 2008

(86) PCT No.: PCT/US2008/001486
§ 371 (c)(1),
(2), (4) Date: Oct. 29, 2010

(87) PCT Pub. No.: WO2008/097527
PCT Pub. Date: Aug. 14, 2008

(65) Prior Publication Data
US 2011/0036171 A1    Feb. 17, 2011

(51) Int. Cl.
*G01N 29/06* (2006.01)
(52) U.S. Cl. .............................. 73/643; 73/642
(58) Field of Classification Search ............ 73/606, 73/642, 643, 587, 599
See application file for complete search history.

(56) References Cited

U.S. PATENT DOCUMENTS

| | | | | |
|---|---|---|---|---|
| 4,137,991 A | * | 2/1979 | Melcher et al. | 181/142 |
| 4,267,732 A | * | 5/1981 | Quate | 73/606 |
| 4,269,067 A | * | 5/1981 | Tynan et al. | 73/643 |
| 4,430,897 A | * | 2/1984 | Quate | 73/606 |
| 4,710,030 A | * | 12/1987 | Tauc et al. | 356/432 |
| 4,909,082 A | * | 3/1990 | Khuri-Yakub et al. | 73/642 |
| 4,938,216 A | * | 7/1990 | Lele | 601/3 |
| 5,431,055 A | * | 7/1995 | Takata et al. | 73/618 |
| 5,457,997 A | * | 10/1995 | Naruo et al. | 73/643 |
| 5,615,675 A | * | 4/1997 | O'Donnell et al. | 600/425 |
| 5,706,094 A | * | 1/1998 | Maris | 356/432 |
| 5,748,317 A | * | 5/1998 | Maris et al. | 356/502 |
| 5,748,318 A | * | 5/1998 | Maris et al. | 356/630 |

(Continued)

FOREIGN PATENT DOCUMENTS
JP    10-128236 A    5/1998

OTHER PUBLICATIONS

R.A. Lemons and C.F. Quate, "Acoustic Microscope—Scanning Version", Applied Physics Letters, vol. 24, No. 4, Feb. 15, 1974.

(Continued)

*Primary Examiner* — Peter Macchiarolo
*Assistant Examiner* — Samir M Shah
(74) *Attorney, Agent, or Firm* — Harrington & Smith

(57) ABSTRACT

An optical-acoustic transducer structure includes at least one metal or semiconducting film in which a part of a pump light pulse is absorbed to generate a sound pulse; and at least one dielectric film. The thicknesses and optical properties of the at least one metal or semiconducting film and the at least one dielectric film are selected so that a returning sound pulse results in a measurable change in the optical reflectivity and/or some other optical characteristic of the transducer structure. The transducer structure includes a resonant cavity, and an output surface that is shaped so as to provide no significant focusing of generated sound waves when the sound waves are launched towards a surface of the sample.

60 Claims, 24 Drawing Sheets

U.S. PATENT DOCUMENTS

| | | | | |
|---|---|---|---|---|
| 5,844,684 | A * | 12/1998 | Maris et al. | 356/432 |
| 5,864,393 | A * | 1/1999 | Maris | 356/28 |
| 5,999,847 | A * | 12/1999 | Elstrom | 604/20 |
| 6,025,918 | A * | 2/2000 | Maris | 356/388 |
| 6,038,026 | A * | 3/2000 | Maris | 356/514 |
| 6,317,216 | B1 * | 11/2001 | Maris | 356/496 |
| 6,321,601 | B1 * | 11/2001 | Maris | 73/657 |
| 6,491,685 | B2 * | 12/2002 | Visuri et al. | 606/2.5 |
| 7,089,099 | B2 * | 8/2006 | Shostak et al. | 701/29.6 |
| 7,339,676 | B2 * | 3/2008 | Maris | 356/432 |
| 7,624,640 | B2 * | 12/2009 | Maris et al. | 73/643 |
| 7,782,471 | B2 * | 8/2010 | Maris | 356/630 |
| 7,935,107 | B2 * | 5/2011 | Altshuler et al. | 606/9 |
| 7,942,915 | B2 * | 5/2011 | Altshuler et al. | 607/88 |
| 7,942,916 | B2 * | 5/2011 | Altshuler et al. | 607/88 |
| 2001/0055435 | A1 * | 12/2001 | Biagi et al. | 385/7 |
| 2006/0272418 | A1 * | 12/2006 | Maris et al. | 73/606 |
| 2006/0272419 | A1 * | 12/2006 | Maris et al. | 73/606 |

OTHER PUBLICATIONS

B. Hadiomioglu and C.F. Quate, "Water acoustic microscopy at suboptical wavelengths", Applied Physics Letter 43 (11), Dec. 1, 1983, pp. 1006-1007.

A. Rodriguez Rey, G.A.D. Briggs, T.A. Field and M. Montoto, "Acoustic Microscopy of Rocks", Journal of Microscopy, vol. 160, Pt 1, Oct. 1990, pp. 21-29.

K. Yamanata and Y. Enomoto, "Observation of Surface Cracks with an Acoustic Microscope", Journal of Applied Physics 53 (2), Feb. 1982.

G. Tas, J.J. Loomis, H.J. Maris, A.A. Bailes, and L.E. Seiberling, "Picosecond Ultrasonics Study of the Modification of Interfacial Bonding by Ion Implantation", Applied Physics Letters, vol. 72, No. 18, pp. 2235-2237.

J. Bereiter Hahn, "Scanning acoustic microscopy visualizes cytomechanical responses to cytochalasin D", Journal of Microscopy, vol. 146, Pt 1, Apr. 1987, pp. 29-39.

E.A. Schenk, R.W. Waag, A.B. Schenk and J.P. Aubuchon "Acoustic microscopy of red blood cells", Journal of Histochemistry and Cytochemistry, vol. 36, No. 10, 1988, pp. 1341-1351.

J.A. Hildebrand and D. Rugar, "Measurement of cellular elastic properties by acoustic microscopy", Journal of Microscopy, vol. 134, Pt 3, Jun. 1984, pp. 245-260.

J. Wu, "Acoustical tweezers", J. Acoust. Soc. Am. 89 (5), May 1991, pp. 2140-2143.

V.I. Trigub and A.V. Plotnov, "A Change in the Structure of an Ultrasonically Processes MMA-MAA.Based Photoresist", Technical Physics Letters, vol. 28, No. 6, 2002.

Y. Arata, Yue Chang Zhang; "Intense Sonoimplantation of atoms from gases into metals", Applied Physics Letters, vol. 80, No. 13, Apr. 1, 2002, pp. 2416-2418.

I.V. Ostrovskii, L.P. Steblenko, A.B. Nadtochii, "Ultrasound-Induced Surface Hardening of Dislocation-Free Silicon", Atomic Structure and Nonelectronic Properties of Semiconductors, vol. 34, No. 3, Mar. 2000. pp. 251-254.

* cited by examiner

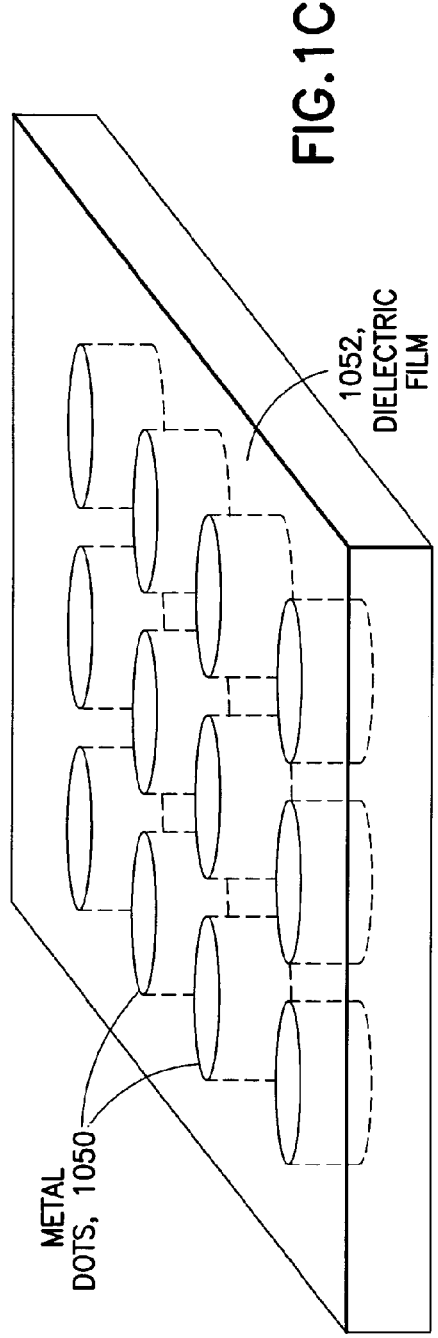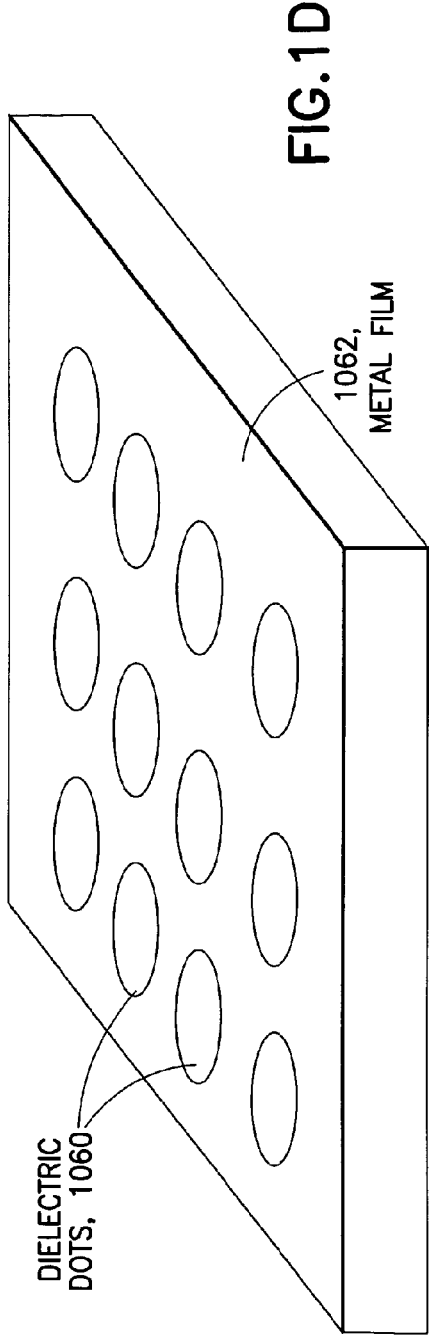

ENHANCED ULTRA-HIGH RESOLUTION ACOUSTIC MICROSCOPE

TECHNICAL FIELD

The exemplary embodiments of this invention generally concern methods and apparatus suitable for use in instruments in which sound waves are used to perform sample analysis operations, and more particularly concern instruments such as, for example, acoustic microscopes.

BACKGROUND

In an acoustic microscope sound is generated in some way and then brought to a focus. The object to be studied is placed at or near the focus and an image of the object can be obtained by moving the object laterally and monitoring the variation of the amplitude and phase of the acoustic waves that are reflected from the object or that are transmitted through the object. Instead of moving the object that is to be imaged, one may hold the object in one place and vary the position of the acoustic focus. The position of the acoustic focus can be changed by moving the position of a lens used to focus the sound.

Conventional acoustic microscopes consist of a transducer to generate sound, and a lens to focus the sound, a coupling medium (usually water) through which the sound propagates to come to a focus, and the sample object. The sound reflected from the object may be collected by the same lens that is used to focus the incident beam or by another lens. To collect sound transmitted through the sample a collection lens is needed on the far side of the sample.

It is usually considered that the first scanning acoustic microscope was built by R. A. Lemons and C. F. Quate, (see "Acoustic Microscope—Scanning Version", Appl. Phys. Lett. 24, 163 (1974)). This used a continuous acoustic wave of frequency 160 MHz, had a resolution of 10 micron, and worked in the transmission mode.

The resolution of an acoustic microscope is determined by the wavelength of the sound that is used and by the numerical aperture of the lens or lenses that are used. To achieve a high resolution, it is necessary to work at the highest possible frequency with a large numerical aperture. According to Briggs, p. 45, the best resolution obtained with water as the coupling medium is described in the work of B. Hadiomioglu and C. F. Quate, Appl. Phys. Lett. 43, 1006 (1983). They used sound pulses of frequency 4.4 GHz and 3 ns duration, with a lens of numerical aperture 0.73 and a radius of 15 micron. The resolution in the linear mode was 0.37 micron and with non-linearity was 0.24 micron. Non-linearity refers to the effect that if the amplitude of the sound near to the focus is sufficiently large, higher frequency harmonics are generated. The presence of these shorter wavelength components improves the resolution. Note that 3 ns at 4.4 GHz corresponds to only 13 cycles.

When the frequency is increased, the attenuation of the sound in water becomes a severe problem. In water, the attenuation in the GHz frequency range varies as the square of the frequency. At 38° C., human body temperature, the attenuation a per unit distance in water is given by $a=0.016\, f^2$ $\text{micron}^{-1}$, where f is the frequency in GHz. In a reflection microscope, it is necessary to have the time duration t of the acoustic pulse less than the round trip time from the lens surface to the sample and back. When sound is generated by an electrically driven piezoelectric transducer, it is very difficult to make t less than a few ns (say 5 ns), and so the acoustic path length has to be at least 8 micron and preferably somewhat longer. A 5 GHz sound wave would be attenuated by 35 dB after traveling 10 micron. Thus, for a given working distance from the lens to the sample object, the attenuation effectively controls the highest frequency that can be used and consequently limits the resolution. Water is the usual choice for a coupling medium because of its low attenuation. There are liquids with lower attenuation (e.g., He, $H_2$, $CS_2$, Hg, Ga), but there are difficulties in working with these materials. For example, He and $H_2$ cannot be used as coupling liquids at room temperature. For biological samples, water is generally the only possible coupling medium.

SUMMARY

The foregoing and other problems are overcome, and other advantages are realized, in accordance with the exemplary embodiments of this invention.

An optical-acoustic transducer structure includes at least one metal or semiconducting film in which a part of a pump light pulse is absorbed to generate a sound pulse; and at least one dielectric film. The thicknesses and optical properties of the at least one metal or semiconducting film and the at least one dielectric film are selected so that a returning sound pulse results in a measurable change in the optical reflectivity and/or some other optical characteristic of the transducer structure.

In another exemplary aspect of this invention there is provided a transducer assembly that comprises a substrate having a top surface for receiving pump light and probe light and a bottom surface; and a transducer structure coupled to the bottom surface, the transducer structure configured to generate sound waves in response to the pump light and comprising an optical cavity having an output surface to direct the generated sound waves towards a sample and to collect sound waves returning from the sample. The output surface is shaped so as to provide no significant focusing of the generated sound waves when the sound waves are launched towards a surface of the sample.

In accordance with further exemplary embodiments of this invention there is provided a processing system, such as a semiconductor wafer processing system, that includes a process controller; a plurality of process stations implementing a process flow on a structure (such as a semiconductor wafer) under direction of the process controller; and at least one opto-acoustic microscope system coupled to the process controller. The at least one opto-acoustic microscope system is operable for determining at least one characteristic of a surface of the structure, and includes a transducer assembly that comprises a substrate having a top surface for receiving pump light and probe light and a bottom surface, and a transducer body coupled to the bottom surface. The transducer body is configured to generate sound waves in response to the pump light and comprises an optical cavity having an output surface to direct the generated sound waves towards the surface of the structure and to collect sound waves returning from the surface of the structure. The output surface is shaped so as to provide no significant focusing of the generated sound waves when the sound waves are launched towards the surface of the structure.

In accordance with still further exemplary embodiments of this invention there is provided at least one method that includes: applying a pulse of pump light to a transducer structure comprising an optical cavity; generating a pulse of acoustic energy within the transducer structure in response to the pulse of pump light; directing the pulse of acoustic energy from the transducer structure towards a surface of a sample, the directed pulse having a substantially planar wave front;

receiving in the transducer structure at least a portion of acoustic energy returning back from the surface; applying a pulse of probe light to the transducer structure; detecting, in cooperation with the optical cavity, the received acoustic energy through a change in at least one characteristic of the probe light; and in response to detecting, determining at least one characteristic of the surface of the sample.

BRIEF DESCRIPTION OF THE DRAWINGS

The foregoing and other aspects of the exemplary embodiments of this invention are made more evident in the following Detailed Description, when read in conjunction with the attached Drawing Figures, wherein:

FIGS. 1A-1D illustrate exemplary embodiments of the invention described in the above-captioned U.S. patent application Ser. No. 11/274,628, where FIG. 1A depicts an embodiment of an opto-acoustic transducer assembly;

FIG. 1B depicts another embodiment of an opto-acoustic transducer assembly;

FIG. 1C shows a first embodiment of a film for detecting a returning sound pulse, the film comprising an array of metal dots surrounded by a dielectric material; and FIG. 1D shows a second embodiment of a film for detecting a returning sound pulse, the film comprising an array of dielectric dots surrounded by a metal.

FIG. 2 shows an enlarged, cross-sectional view of an embodiment of an opto-acoustic transducer assembly;

FIG. 3 shows the opto-acoustic transducer assembly of FIG. 2 disposed over a sample surface having a featured (patterned) surface;

FIG. 4 is a graph that shows the temporal separation of two sound echos received from the patterned sample surface shown in FIG. 3;

FIG. 5 shows the patterned surface of the sample of FIG. 3 in greater detail, and is useful in understanding the graph of FIG. 4;

FIG. 6 shows another exemplary patterned surface of a sample;

FIG. 7 shows an acousto-optic microscope system in combination with a simulator;

FIG. 8 shows the opto-acoustic transducer assembly of FIG. 2 disposed on a sample surface characterized by the presence of at least one film layer;

FIG. 9 shows an exemplary embodiment of the opto-acoustic transducer assembly of FIG. 2 formed onto, or otherwise optically coupled to, a terminal end of an optical fiber through which pump and probe light is delivered; and FIG. 10 shows the acoustic lens positioned above the sample surface at a working distance, as well as an intervening coupling medium.

FIG. 11 shows an enlarged, cross-sectional view of an embodiment of an opto-acoustic transducer assembly having an optical cavity containing films of dissimilar metals;

FIGS. 12 and 13 each show an enlarged, cross-sectional view of an embodiment of an opto-acoustic transducer assembly having an optical cavity in which there is one metal film, the dielectric layer, and a dielectric Bragg mirror or reflector;

FIG. 14 shows an enlarged, cross-sectional view of an embodiment of an opto-acoustic transducer assembly having an optical cavity formed as, or that contains, an air gap (that may be tunable);

FIGS. 15 and 16 each show an enlarged, cross-sectional view of an embodiment of an opto-acoustic transducer assembly having a patterned film that contacts the coupling fluid, while

FIG. 17 shows an enlarged, cross-sectional view of an embodiment of an opto-acoustic transducer assembly used to make a measurement on a sample surface having a single upstanding feature, as opposed to an array of repeating features such as those shown in FIGS. 15 and 16;

FIG. 18 shows an enlarged, cross-sectional view of an embodiment of an opto-acoustic transducer assembly used to make a measurement on a sample surface, where the pump light propagates through to the sample surface and generated sound waves that propagate back to the transducer assembly;

FIG. 19 shows an enlarged, cross-sectional view of an embodiment of an opto-acoustic transducer assembly having a DBR in contact with a metal film; and FIG. 20 illustrates a sample having a surface profile characterized by a series of equally spaced trenches.

DETAILED DESCRIPTION

Reference may be made to U.S. Patent Application No. 2006 0272418-A1, U.S. Patent Application No. 2006 0272419-A1, and to WO2006/132862 A2, the disclosures of which are incorporated by reference as if fully restated herein.

In exemplary embodiments sound is generated when a light pulse, a "pump" light pulse, is absorbed in a material. The sound is then brought to a focus on the surface of a sample by the use of an acoustic lens. The sound travels from the lens to the sample through a coupling medium, which may be water or another suitable liquid. The sound is reflected from the surface of the sample and returns through the coupling medium to the acoustic lens. After the sound is collected by the acoustic lens it is detected by the use of another light pulse, a "probe" light pulse, which is delayed in time relative to the pump light pulse. A number of different embodiments for the acoustic lens may be realized, and a number of different materials may be used for the acoustic lens and the material in which the pump light pulse is absorbed. An acoustic microscope in which the sound is transmitted through a substrate instead of being reflected from it may also be employed. An optical cavity may also be employed to enhance the detected signal. A number of different applications, including the use of the system to modify the properties of a sample, may also be used.

FIGS. 1A-1D illustrate exemplary embodiments of the invention described in the above-captioned U.S. patent applications.

Figure 1A:
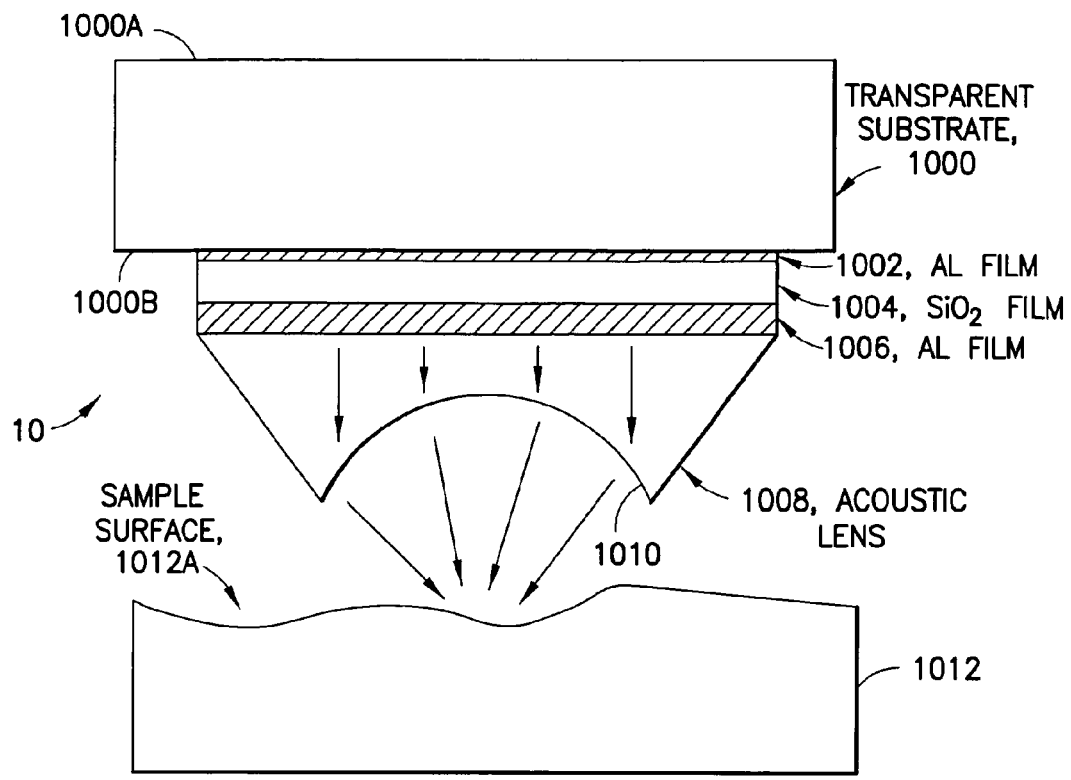

For the purposes of detecting the returning sound pulse it may be advantageous to provide an opto-acoustic transducer 10 (also referred to herein as an AOTA 10) as a multilayer structure, although the use of single film layer embodiments is also advantageous. One non-limiting example is shown in FIG. 1A. On the lower surface 1000B of a substrate 1000 are deposited, in sequence, films of a non-dielectric material, such as a metal (e.g., aluminum) 1002, a dielectric material (e.g. silicon dioxide or a polymer) 1004 and a second non-dielectric material such as the same or another metal 1006. An acoustic lens 1008 is located below the second non-dielectric film 1006, and the pump and probe light pulses are directed down from the top surface 1000A of the substrate 1000. The acoustic lens 1008 includes a concave region 1010 for focusing the acoustic energy. The upper Al film 1002 is made sufficiently thin so as to transmit an appreciable fraction of the light pulses. Sound is generated when the pump light is absorbed in either or both of the Al films 1002, 1006. Probe light that passes through the upper Al film 1002 is reflected back and forth multiple times within the SiO$_2$ film 1004 between the upper and lower Al films, 1002, 1004, effectively setting up a standing wave. As may be appreciated, the Al/SiO$_2$/Al structure defined by films 1002, 1004, 1006 acts in a manner similar to a Fabry-Perot interferometer. The Al/SiO$_2$/Al structure defined by films 1002, 1004, 1006 may be considered to form an optical micro-cavity. If the thickness of the SiO$_2$ layer is appropriately chosen, the reflection of light from the Al/SiO$_2$/Al structure is very sensitive to small changes in the thickness and/or refractive index of the SiO$_2$ layer 1004. A returning sound pulse causes a change in the thickness of the SiO$_2$ layer 1004 and modifies the refractive index of the SiO$_2$ layer 1004. Thus when a sound pulse returns from the surface 1012A of the sample 1012 and enters the SiO$_2$ layer 1004, a potentially large change occurs in the reflection of the probe light pulse. This type of structure thus provides a sensitive means for the detection of the returning sound pulses.

To fabricate the micro-cavity just described, the thickness of the SiO$_2$ layer 1004 is preferably made to be approximately equal to an integer number of half wavelengths of the probe light in the SiO$_2$. Thus, if the wavelength of the probe light in vacuum is 600 nm and the refractive index of the SiO$_2$ layer is 1.46, the thickness of the SiO$_2$ layer is made to be about 205 nm, or about 410 nm, etc.

Under the conditions just described the phase of the reflected probe light also undergoes a large (and detectable) change when sound travels through the SiO$_2$ layer 1004.

There are a number of possible and useful variations of the embodiment shown in FIG. 1A.

Figure 1B:
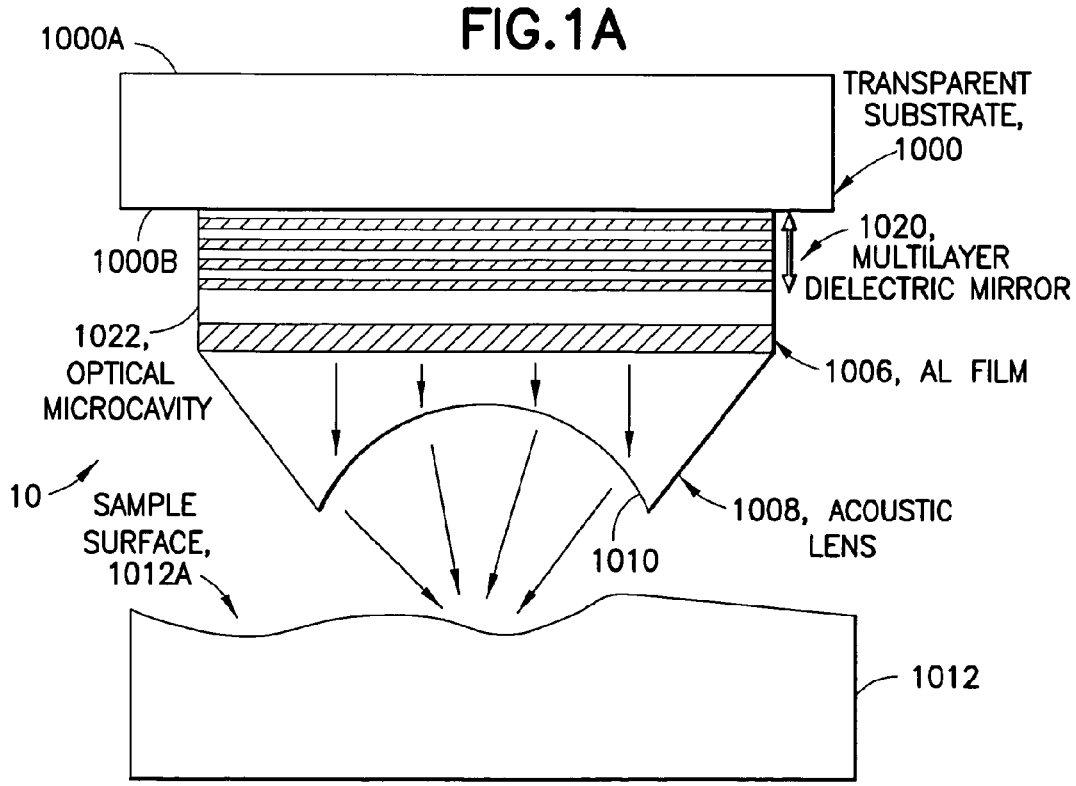

As one non-limiting example, the upper Al film 1002 may be replaced by a multilayer dielectric mirror structure 1020 as in FIG. 1B. The multilayer dielectric mirror structure 1020 acts as a Bragg-type reflector for the incident light pulse(s). An optical micro-cavity layer 1022 disposed between the multilayer dielectric mirror structure 1020 and the Al film 1006 includes a layer of SiO$_2$, or other dielectric material, of appropriate thickness. When the returning sound pulse enters the optical micro-cavity layer 1022 it changes the thickness and refractive index of this layer. This results in a potentially large change in the optical reflection of the overall structure consisting of the multilayer dielectric mirror structure 1020, optical micro-cavity layer 1022 and the Al film 1006. In practice, the multilayer dielectric mirror structure 1020 may have, as non-limiting examples, from 2 to 16 alternating dielectric films (e.g., SiO$_2$ and TiO$_2$). The film thicknesses and numbers of films are preferably tuned in relation to the probe beam wavelength. In addition to the change in the reflectivity due to the effect of the sound on the material in the optical micro-cavity, there is also a contribution to the reflectivity change of the overall structure due to: 1) the change in the refractive index and thickness of the materials composing the multilayer dielectric mirror 1020 when the sound passes through the mirror; and 2) the change in the optical properties and thickness of the Al film when the sound passes through the Al film.

In general, the dielectric mirror structure 1020 is constructed so as to contain alternating layers of two materials 1 and 2 with different refractive indices n1 and n2. In the embodiment shown in FIG. 1B, the thickness of each layer of material 1 is the same throughout the structure, and the thickness of each layer of material 2 is also the same throughout the structure. However, it may be advantageous to use a dielectric mirror structure 1020 in which the thicknesses of all or some of the layers of material 1 (and all or some of the layers of material 2) are different. For example, the thickness of each successive layer of material 1 may be larger than the thickness of the preceding layer by a selected amount. In this way, it is possible to construct a dielectric mirror that yields a larger change in the reflectivity of the overall structure as a result of the arrival of the sound pulse.

It is noted that by using different wavelengths for the pump and probe light pulses it is possible to make the multilayer dielectric mirror structure 1020 exhibit different transmission and reflection characteristics for the pump and probe light pulses.

For the purpose of generating and detecting the returning sound pulse it may be advantageous to use a laterally patterned film or films, with individual structural features possessing dimensions which are less than the wavelength of light employed. For example, and referring to FIG. 1C, such a film may include an array of metal dots 1050 surrounded by dielectric material 1052, or an array of dots 1060 composed of dielectric material filling apertures in a metal film 1062, or other finely nano-textured materials with size in the range of, for example, 1 nm to 100 nm. As non-limiting embodiments, the metal in FIGS. 1C and 1D may include one or more of Al, Au or As, while the dielectric material may include a polymer or an oxide. The dot structures 1050, 1060 can be formed using micro-nanofabrication techniques such as those based on electron-beam lithography, through the use of self-assembled arrays of nanoparticles such as quantum dots, or by conventional photolithographic techniques, and may include as examples etching and backfilling etched voids with a metal or a dielectric, or may include an implantation process. Such a patterned film can be prepared so as to have a reflection and absorption coefficient that has a favorable value for use with the exemplary embodiments of this invention.

In operation, a returning sound pulse operates to change the optical properties of the metal and the dielectric components of the film, and the change in the optical reflection induced by the returning sound pulse can be made to have a large value. The structure may be designed for optimizing the absorption of incident optical pump light at specific wavelengths so as to enhance the generation of the acoustic pulses. As non-limiting examples the dots can be made to have a height of about 100 nm or less, and a diameter of about 100 nm or less.

In the embodiments discussed thus far in relation to FIGS. 1A-1D, a hemispherical acoustic lens focusing element 1010 can have a radius of, as a non-limiting example, approximately 0.5 um, and may be fabricated into sapphire (or comparable material) by a process that includes, as an example, electron beam grey scale lithography and dry etching.

Operation of the acoustic microscope in a further mode may be explained by reference to FIG. 2, where it is desirable to increase the radius of curvature of the acoustic lens concave region 1010 while holding the distance to the sample 1012 fixed. In this case the acoustic focus (AF) may be considered to move to a position that is below, possibly substantially below, the sample surface 1012A. If the radius of curvature of the acoustic lens 1010 is sufficiently large one may consider that a substantially planar acoustic wave impinges onto the surface 1012A of the sample 1012. The amplitude of this acoustic wave is essentially constant over the area of the sample surface 1012A beneath the acoustic lens 1008 (ignoring diffraction effects), and if the sample surface 1012A is flat, the wave arrives at all points on the sample surface 1012A at the same time. This wave then returns to the acoustic lens 1008 in such a manner that the wave reaches each point on the surface of the acoustic lens element 1010 at the same time. Note that FIG. 2 also shows the coupling medium 1050, such as water, interposed between the acoustic lens 1008 and the sample surface 1012A.

As was already noted, the element that is referred to here as a "lens" may in fact have a substantially flat surface, i.e., the "concave region" 1010 may in fact be optically flat or substantially flat.

Figure 10:
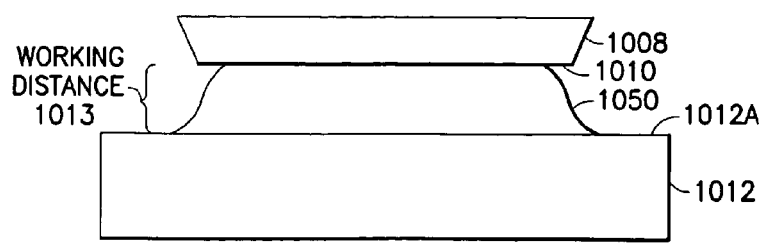

FIG. 10 shows the acoustic lens 1008 positioned above the sample surface 1012A at a working distance 1013. As a non-limiting example, the working distance 1013 may be in a range of about 0.05 microns to about 50 microns, and may be related to one or more characteristics (e.g., viscosity, surface tension) of the coupling medium 1050.

Note that for the case where the surface 1010 of the acoustic lens is substantially flat, the acoustic focus may be considered to be essentially at infinity, and is thus clearly substantially below the surface 1012A of the sample 1012.

Figure 2:
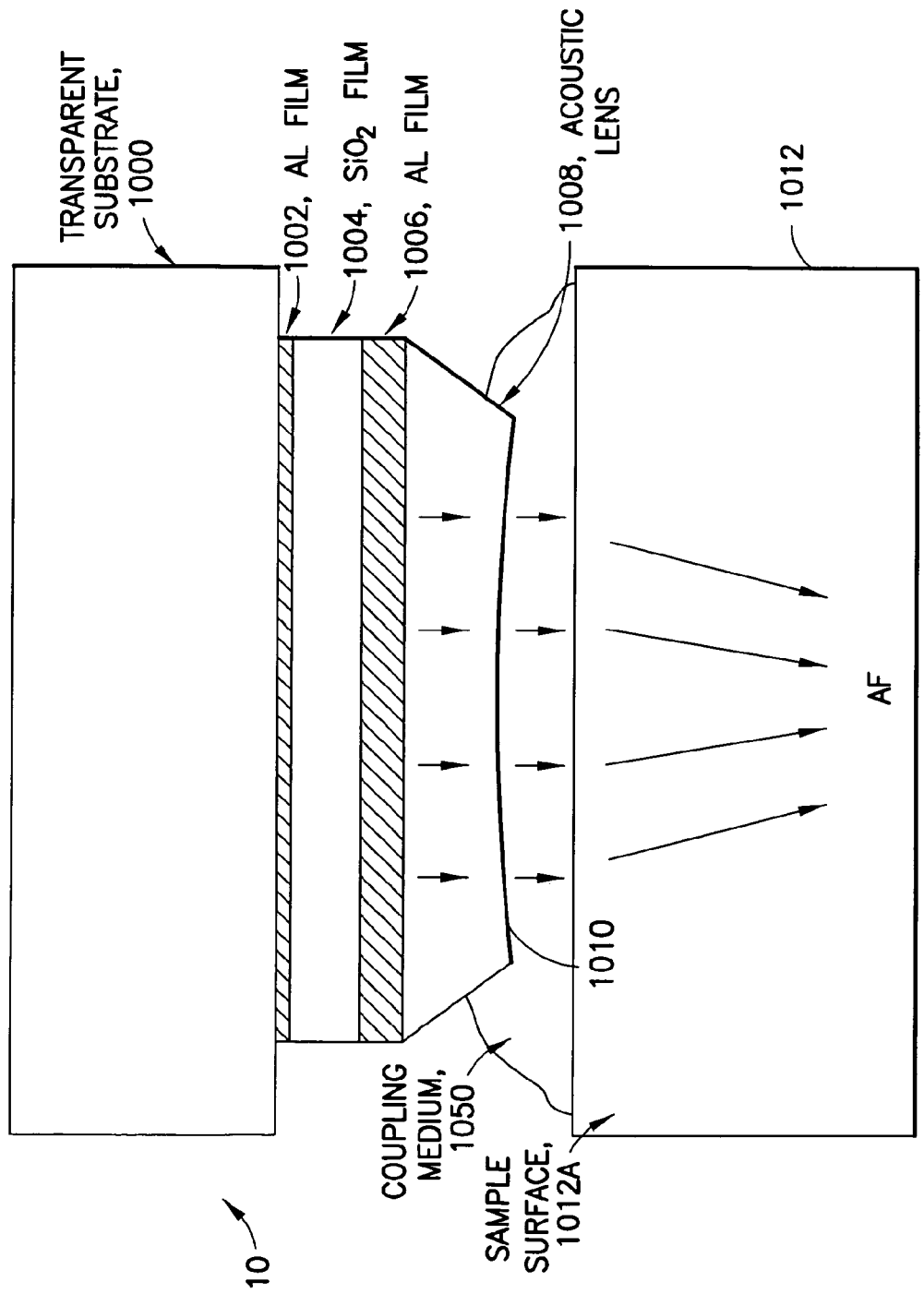
FIGS. 2-10 illustrate exemplary embodiments of the invention described in the above-captioned U.S. Provisional Patent Application No. 60/899,860, where

Continuing with the description of FIG. 2, the returning wave passes through the lens material into the optical cavity (or other structure) in which it is detected. Since all parts of the front of the acoustic wave reach the region in which sound is detected at the same time, the sound is detected as a single echo that arrives at a discrete time.

Note that FIG. 2 has been described by way of convenience, and not as a limitation, in the context of the acoustic lens transducer 10 shown in FIG. 1A, and note further that another acoustic lens assembly, such as the shown in FIG. 1B, could be employed as well.

Figure 3:
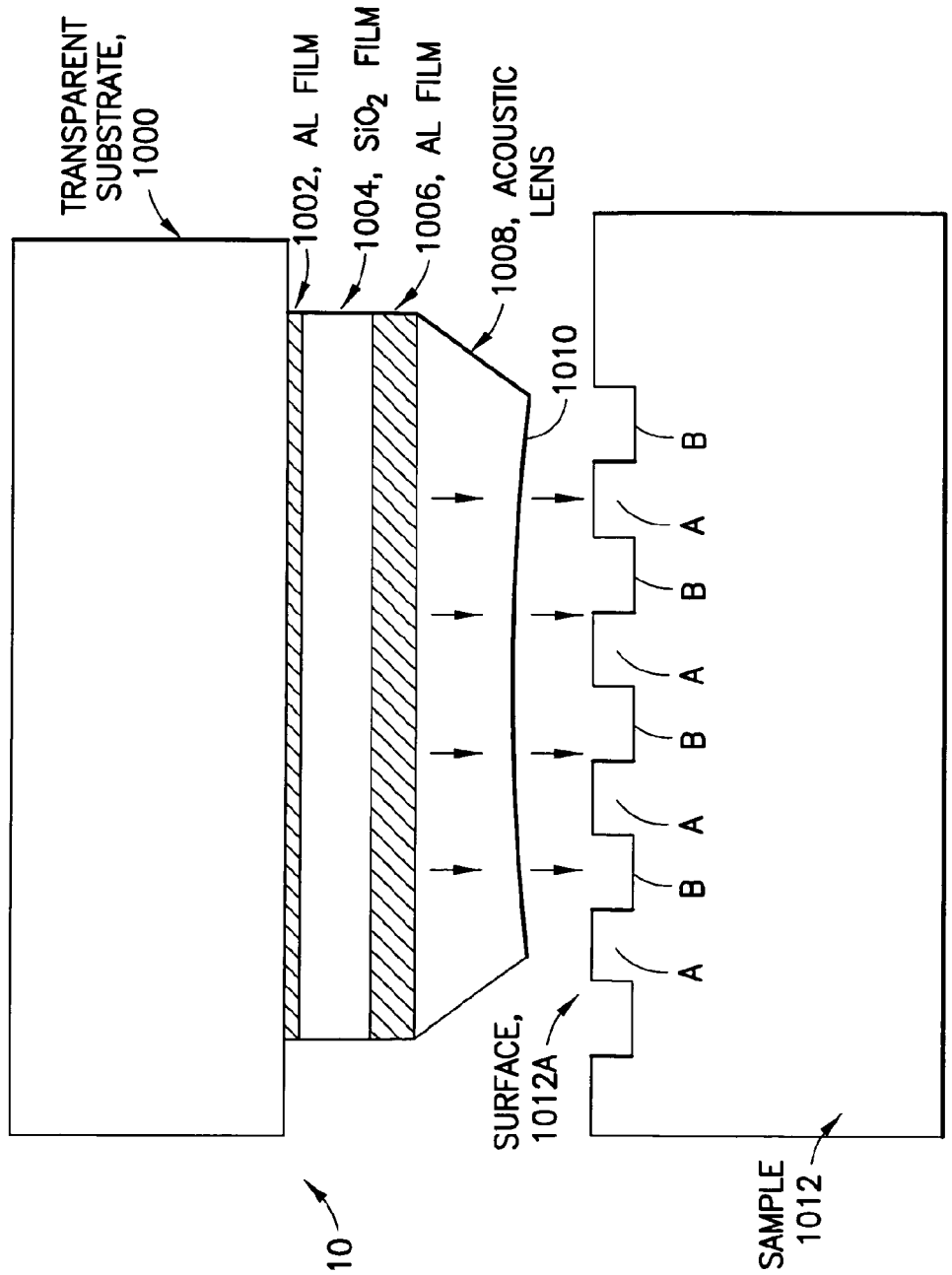
Figure 4:
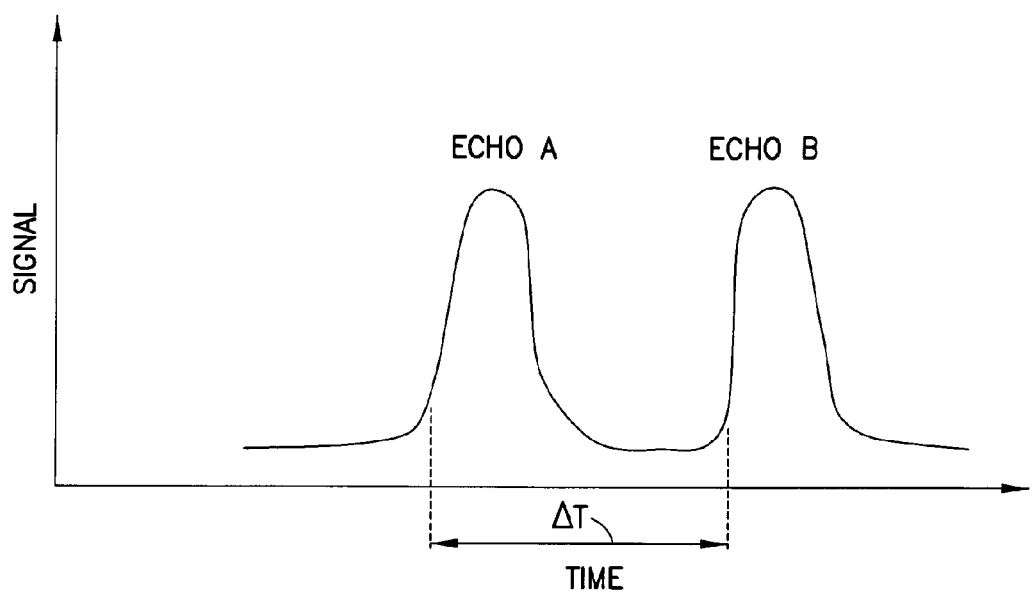

Consider now the application of the exemplary embodiments to the study of a sample 1012 of the type shown in FIG. 3, where the sample surface 1012A is patterned so as to have an irregular (non-planar) surface characterized by upstanding features. For this particular type of sample 1012 some part of the acoustic pulse is reflected from the regions of the surface 1012A labeled as A and some part is reflected from the regions of the surface labeled B. The sound reflected from the A regions returns and reaches the region in which sound can be detected earlier than the sound that is reflected from the B regions. Thus, the acoustic response as measured by the probe light pulse will contain two acoustic echoes (Echo A and Echo B, corresponding to surface regions A and B, respectively) that are separated in time as shown in FIG. 4. The separation in time is given by the relation:

$$\tau = 2h/v,$$

where h is the depth of the regions B relative to the regions A and v is the velocity of sound in the acoustic coupling medium 1050 between the lower surface 1010 of the acoustic lens and the sample surface 1012A.

Figure 5:
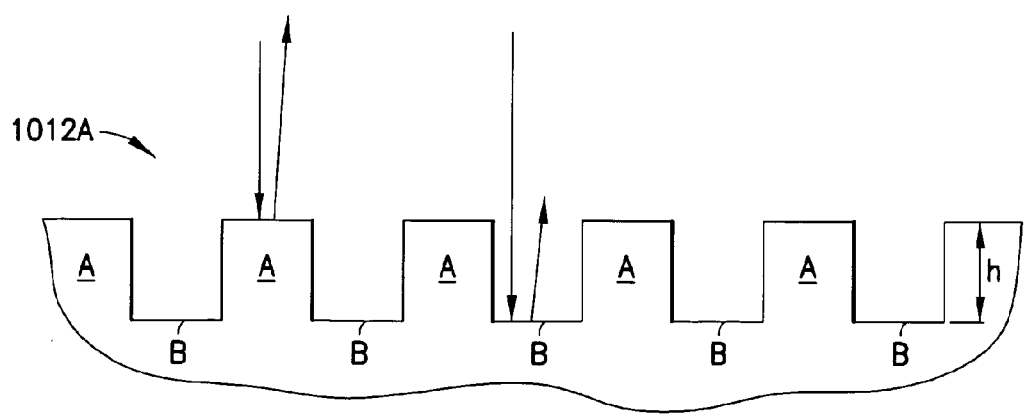

The geometry of the sample surface 1012A is shown in more detail in FIG. 5, which clearly illustrates that the sound reflected from regions B returns later than the sound reflected from regions A.

A measurement of the time difference (delta T in FIG. 4) between the two echoes can be used to determine the difference in height of the A and B regions. In water (one exemplary coupling medium 1050) the sound velocity is approximately 15 Å/ps (15 Ångstroms per picosecond) and, thus, if the difference in height is 1000 Å, the difference in the time of arrival of the two echoes will be 130 ps (the round trip time of the sound wave striking the B regions as compared to the sound wave striking the A regions).

Figure 6:
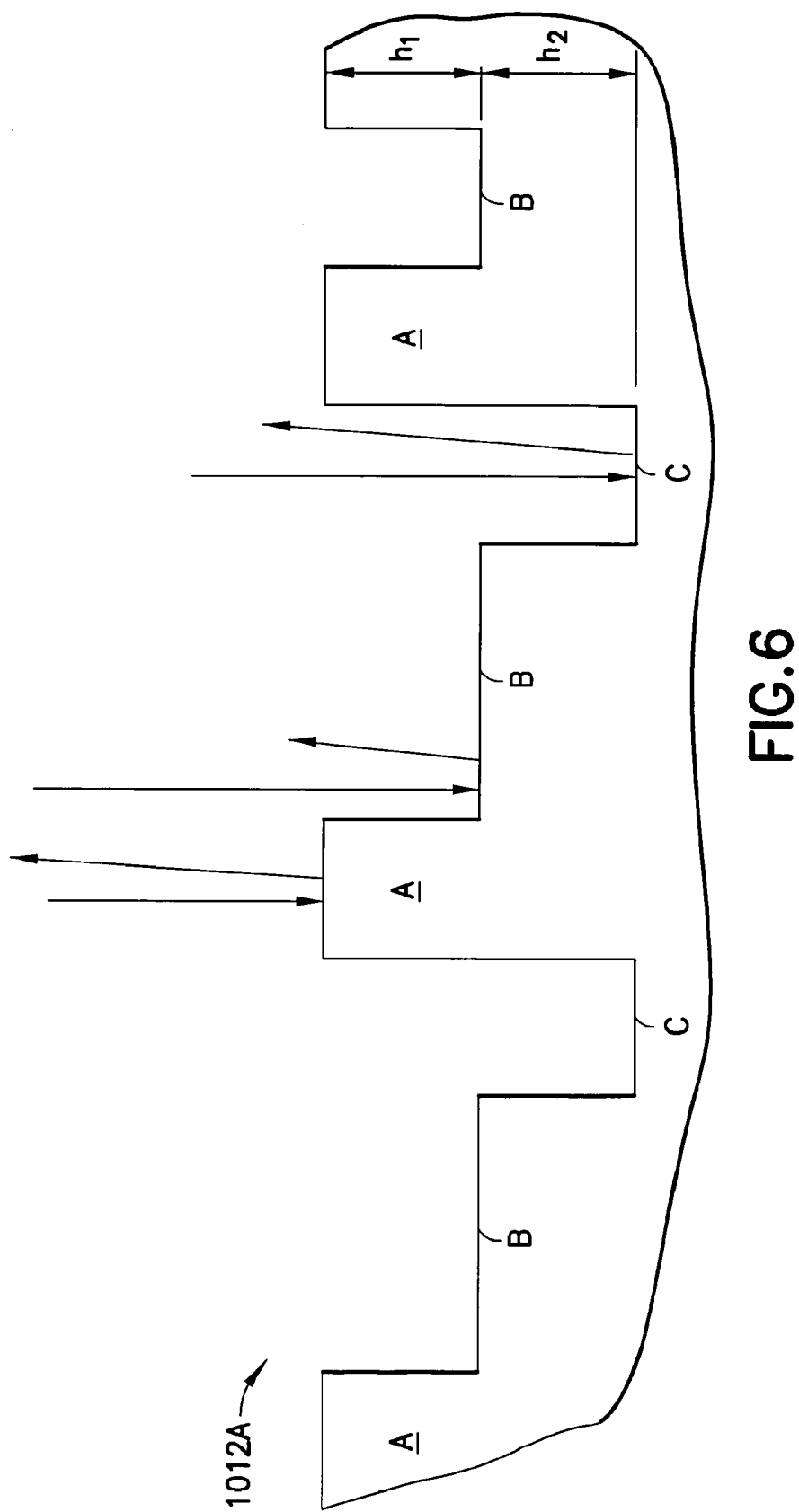

In one type of sample 1012 of interest the B regions may be trenches running across the sample surface 1012A, or they may be one or more isolated "pits" or voids in the sample surface 1012A. Alternatively, the A regions may be ridges running across the sample surface 1012A or islands standing above the B regions. The sample surface 1012A may include more than two levels, e.g., three levels separated by heights $h_1$ and $h_2$, as shown in FIG. 6. For the sample shown in FIG. 6 three distinct echoes are detected, enabling the different heights $h_1$ and $h_2$ to be determined.

It should be noted that the fraction of the total area of the sample which is at the height of A and which is at the height of B affects the relative height (amplitude) of the acoustic echoes. Thus, the relative heights of the echoes can be used to determine the fraction of A regions to B regions. For example, an area that has a particular height may be as small as about 1% of the total area and still be detectable.

Consider now a sample in which the A region of the sample surface and the B region of the sample surface are composed of different materials (e.g., a metal and a dielectric, respectively). Let $f_A$ be the fraction of the area that is region A and let $f_B$ be the fraction of the area that is region B, and assume that the values of $f_A$ and $f_B$ are known. In this case a measurement of the relative heights of the echoes arising from areas of the A and B regions can be used to determine the relative values of the acoustic impedances of A and B. The acoustic impedance Z of a material is equal to the product of the density ρ and the sound velocity v. Thus, for example, if the sound velocity of A, and the densities of A and B are known, then the sound velocity of B can be found.

In the case that the depth of the trenches on the sample surface 1012A is small, it may not be possible to detect two distinct echoes that are clearly separated in time (as in FIG. 4). However, in this situation one may perform a numerical simulation of the expected acoustic signal. The results of the simulation are then compared with the measured acoustical signal, and the input parameters to the simulation, such as the trench depth and the fraction of the area covered by the trenches, and are adjusted to obtain a best fit between the result of the simulation and the actual measurements. This simulation-based approach may be employed as well with more complex samples in which the surface 1012A contains a distribution of steps and trenches with different heights and depths. Again, the measured acoustic signal can be compared with that calculated by means of a simulation and the input parameters to the simulation adjusted so as to obtain a best fit.

Figure 7:
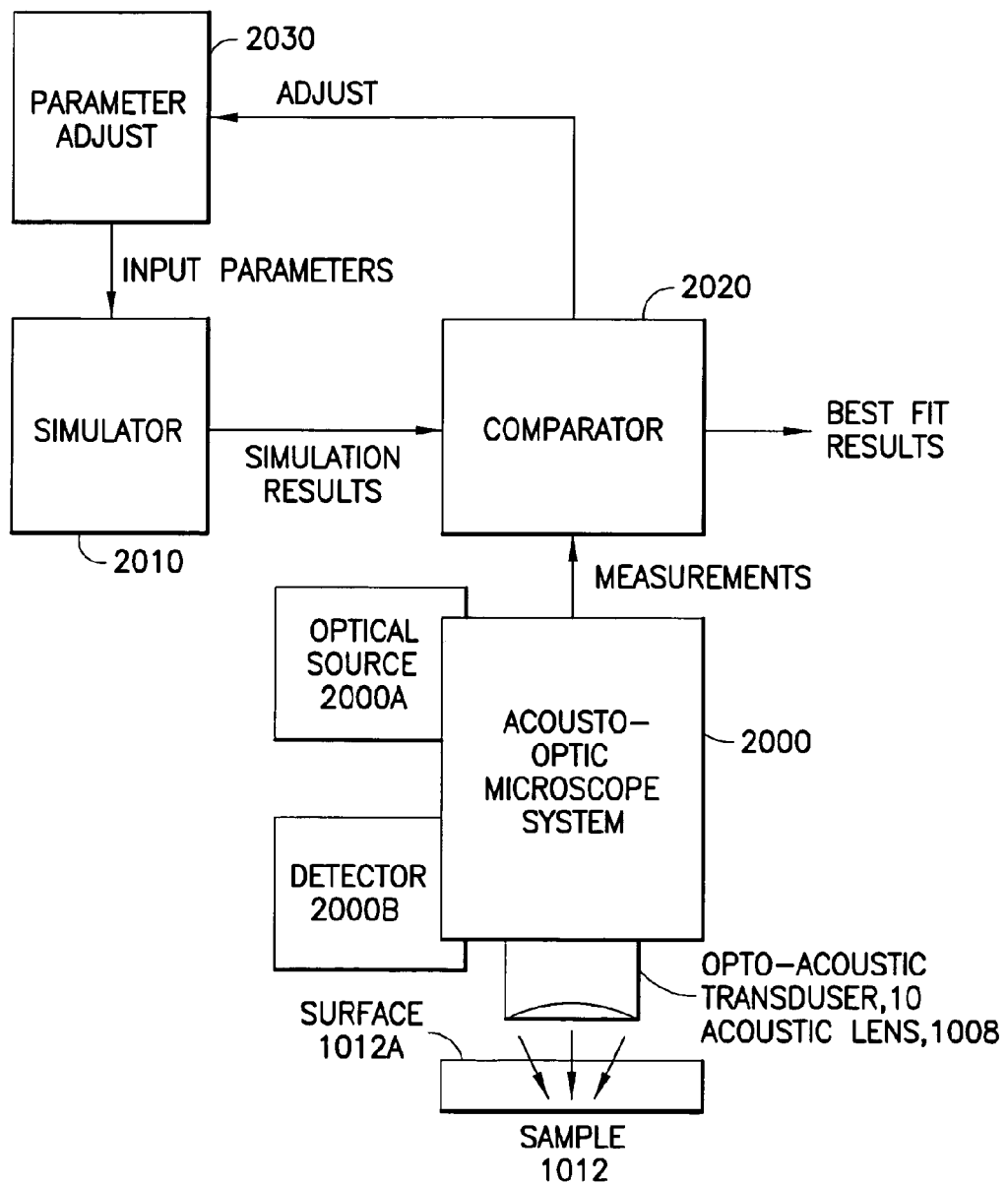

Reference in this regard can be made to FIG. 7 for showing the transducer 10 assembly including the acoustic lens 1008 operated with an acousto-optic microscope system 2000. The acousto-optic microscope system 2000 is assumed to include one or more light sources 2000A (e.g., lasers) for generating the pump and probe light pulses, one or more detectors 2000B suitable for detecting at least one characteristic of the returning probe light (e.g., detecting one or more of the intensity and/or the polarization state of the returning probe light), as well as any necessary signal processing circuitry, and possibly also means for causing relative motion between the acoustic lens 1008 and the sample surface 1012A (e.g., an X-Y, X-Y-Z positioning stage to scan the sample surface). A simulator 2010, such as one embodied as computer program code stored in a memory of a computer, such as a PC, outputs sample-related simulation results to a comparator 2020 that also receives measurements made by the acousto-optic microscope system 2000. Based on the result of the comparison the comparator 2020 sends one or more adjustment commands to a parameter adjustment block 2030 for varying a value of one or more of the input parameters to the simulator 2010. This process may continue in an iterative fashion until a best fit is achieved between the simulation results and the results of the measurements, at which time the best fit results (and possibly including the current values of the parameters) is output. These best fit results will be those, ideally, that most closely describe the characteristics of the sample and sample surface 1012A, such as the sizes and area distributions of surface features, such as (as non-limiting examples) trenches, pits, voids, pedestals, ridges and islands. Note that the simulator 2010, the comparator 2020 and the parameter adjustment block 2030 may in practice all be resident in a single computer system, such as one that controls and/or monitors operation of the acousto-optic microscope system 2000.

As such, it can be appreciated that an aspect of the exemplary embodiments of the invention is the acousto-optic transducer assembly 10 that has an output coupled to means for adjusting input parameters to the simulator 2010, based on acoustic signals detected from the sample 1012, to obtain best fit parameters indicative of a surface topography of the sample.

Note that it is also within the scope of the exemplary embodiments of the invention to test the quality of a sample 1012 by making a measurement of the acoustic signal returning from the sample 1012 and to then compare the measurement with a measurement made from at least one sample that is known to have a desired geometry and/or mechanical properties (e.g., a known good or reference sample).

Figure 8:
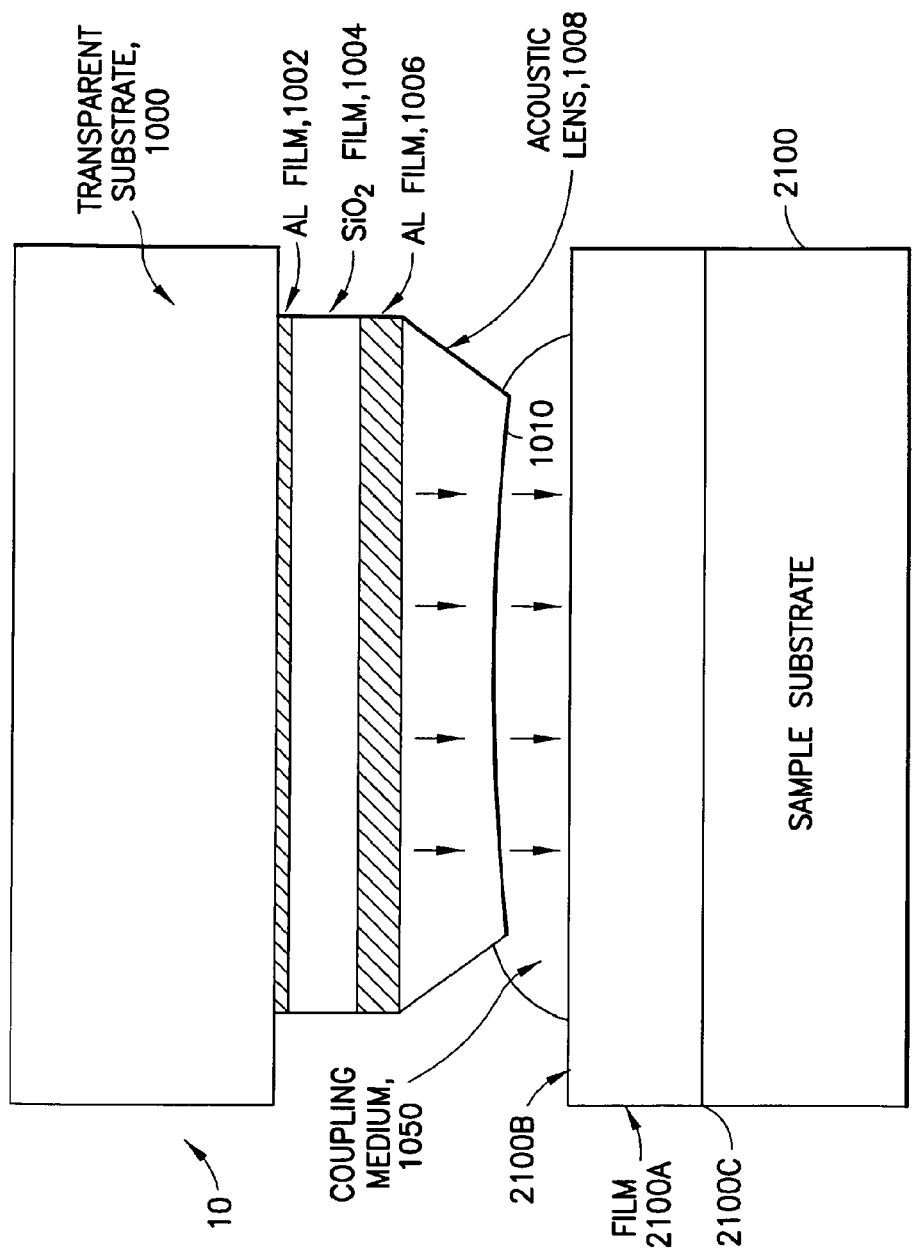

It is also within the scope of the exemplary embodiments to measure the properties of a film, or films, 2100A deposited onto a sample substrate 2100, as shown in FIG. 8. For a substantially planar film 2100A a first acoustic'echo (echo 1) arises from the reflection of the sound at the interface between the coupling medium 1050 and the top surface 2100B of the film 2100A. A second echo (echo 2) then arises from the sound that enters the film 2100A and is reflected at the interface 2100C between the film 2100A and the substrate 2100. The time between the echoes 1 and 2 can be used to determine the thickness of the film 2100A.

For example, and referring again to FIG. 4, assume that the echo A corresponds to echo 1 (from the interface between the coupling medium 1050 and the top surface 2100B of the film 2100A), and that the echo B corresponds to the echo 2 (from the film/substrate interface 2100C). In this case then the value of delta T is thus clearly correlated with the thickness of the film 2100A.

Note further that the relative amplitudes of the two echoes can be used to estimate the quality of the bond between the film 2100A and the substrate 2100. For example, if the film 2100A is poorly bonded to the substrate 2100, then the echo 2 will typically be larger in amplitude than would be expected based on a theoretical calculation using the known laws of acoustics and the assumption of perfect bonding at the interface 2100C. The increase in the amplitude of the echo 2 over what would be expected based on the theoretical calculation (e.g., as a component of a simulation), or based on the amplitude measured from at least one known-good (reference) sample, can thus be correlated with the actual quality of the interface bond between the film 2100A and the substrate 2100.

The use of these exemplary embodiments of the invention provides advantages as compared to conventional approaches, such as in picosecond ultrasonics (PU).

For example, in PU light is absorbed directly in the sample in order to generate sound, whereas in the method in accordance with the exemplary embodiments of the invention the separate acousto-optic transducer 10 is used to generate the sound, thereby enabling transparent samples to be studied.

Further by example, in PU the pump and probe light beams interact directly with the sample, whereas in the exemplary embodiments of this invention the separate transducer 10 is used to generate and to detect the sound.

It should be noted that the high frequency Fourier components of the sound pulse can be strongly absorbed in the coupling medium 1050, resulting in a broadening of the acoustic pulse. As such, the exemplary embodiments of the invention may be preferred for use with other than very thin films and coatings, e.g., other than films of thickness below several hundred Ångstroms. However, for the evaluation of very thick films, e.g., of thickness of about 1 micron or greater, it is possible to increase the thickness of the coupling medium 1050 without appreciably lowering the accuracy with which the film thickness can be determined. This effective increase in the working distance between the opto-acoustic transducer 10 and the sample surface 1012A also increases the speed with which the sample surface 1012A may be scanned.

There are a number of possible design approaches for the transducer 10. These include, but are not limited to, the following exemplary and non-limiting embodiments.

Figure 9:
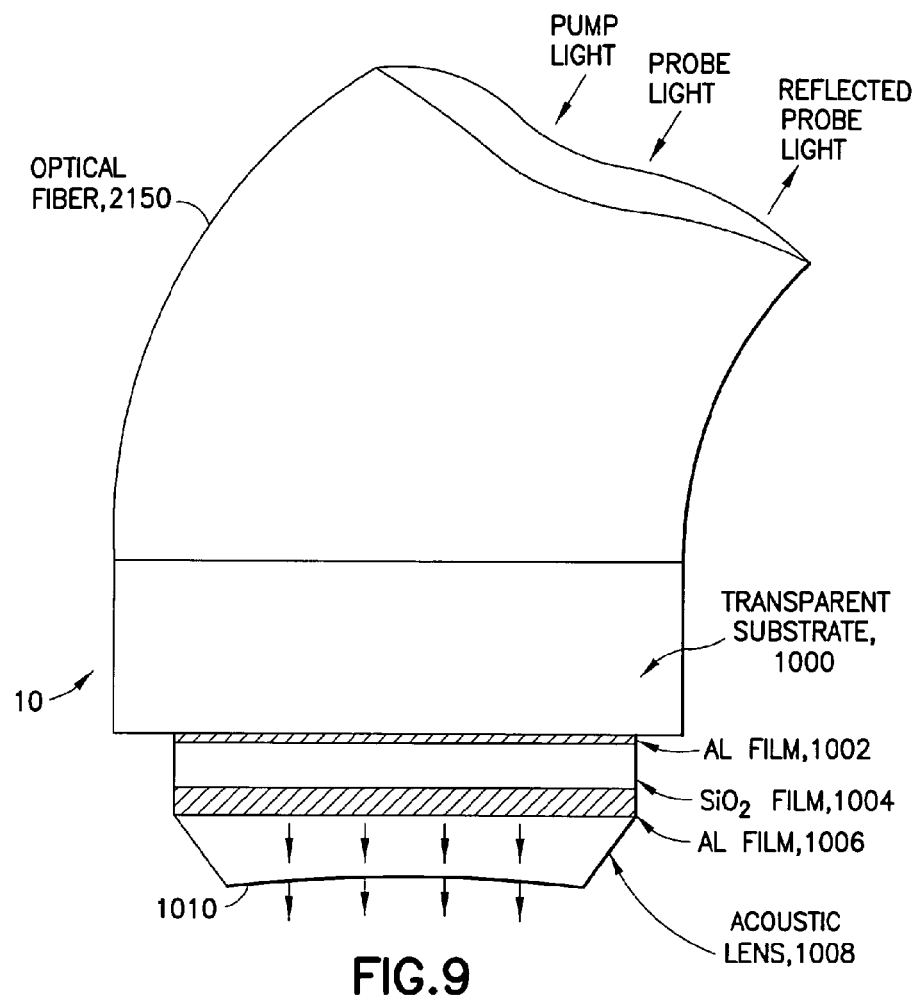

First, and referring to FIG. 9, at least one of the pump and probe light may be delivered by an optical fiber 2150, and the transducer 10 may in this case be formed onto, or otherwise optically coupled to, a terminal end of the optical fiber 2150. Note that reflected probe light may be delivered through the same fiber 2150 to detection electronics and signal processing circuitry that forms a part of the acousto-optic microscope system 2000 shown in FIG. 7.

Second, films of large area may be deposited onto the surface of a transparent sample 1012, and the pump light may be applied to a large area (e.g., a spot 30 microns in diameter), possibly encompassing the entire surface area of the sample 1012, while the probe light is applied to a smaller area. The probe light may be scanned over the sample surface 1012A (over the film surface in this case) in order to make a map of sample properties.

Note that while described above in the context of the generation and reception of "sound waves", this is not intended to imply that the sound waves would be in the audible range normally associated with human hearing.

Note further that any reference herein to a detectable change in the probe light that is output from the opto-acoustic transducer assembly should be implied to encompass any change that is detectable. For example, while a measured characteristic of the probe light may preferably be a change in the intensity of the probe light output from the opto-acoustic transducer assembly, it is also within the scope of the exemplary embodiments of the invention to measure (e.g., in the acousto-optic microscope system 2000 of FIG. 7), the change in some other characteristic(s) of the probe light after it has been returned from the opto-acoustic transducer assembly 10. These other characteristics may include, but need not be limited to, the intensity of transmitted probe light, the phase of the reflected probe light, the direction of the reflected probe light, and the polarization of the reflected probe light. The detector(s) 200B are thus assumed to be responsive to the desired property or properties of the reflected probe light that are desired to be measured.

Described now are further exemplary embodiments of this invention.

It is first noted that one advantage of providing an optical cavity in the transducer assembly is that by making the cavity resonant more energy is absorbed than would be absorbed in a single metallic film. Resonant means in this context that the relation between the wavelength of the light and the width of the dielectric layer is such that a standing optical wave is set up within the cavity. However, light is absorbed in both metal films and consequently two sound pulses are generated at essentially the same time, but at different locations in the structure, which may make the analysis of the measured signal from the returning sound more complex.

In accordance with this exemplary embodiment of the invention, the problems associated with the generation of two sound pulses can be reduced by using different materials for the two metal films. For example, one film could be aluminum and the other copper. Both of these metals have a high reflectivity and so can be used to make an optical cavity with a reasonably high Q. However, the absorption of light in aluminum is considerably larger than in copper, so more light would be absorbed in the aluminum film and the sound pulse generated in that film would be significantly larger than the sound pulse generated in the copper film. As a result it may be a sufficiently good approximation to ignore the sound pulse generated in the copper film. In designing a structure of this type it is also advantageous to choose the materials and layer thicknesses so that acoustic reflections are as small as possible. This is so that the sound pulse, or pulses, that are generated by the pump light do not undergo reflection within the structure, thereby producing additional sound pulses that would make the analysis more complicated.

Figure 11:
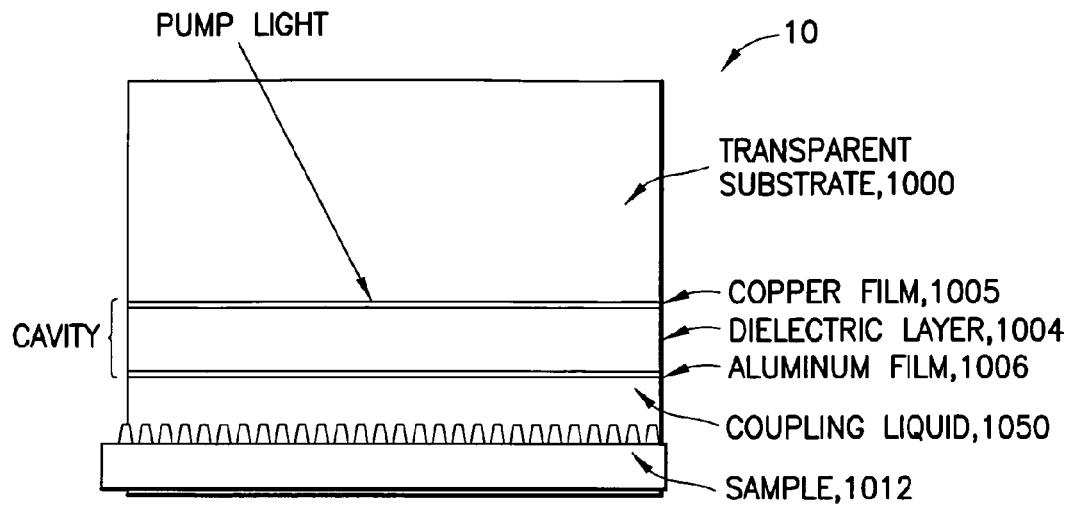
FIGS. 11-20 illustrate exemplary embodiments of this invention, where

An example of the transducer 10 having this type of optical cavity is shown in FIG. 11, where a copper film 1005 bounds one end of the cavity, and where the aluminum film 1006 bounds the other end. Of course, the use of copper and aluminum films is not meant as a limitation upon this invention. In general, this embodiment employs films comprised of two dissimilar reflective materials (e.g., metal-containing materials), where one material is less absorptive of the pump light wavelength(s) than the other material.

Figure 12:
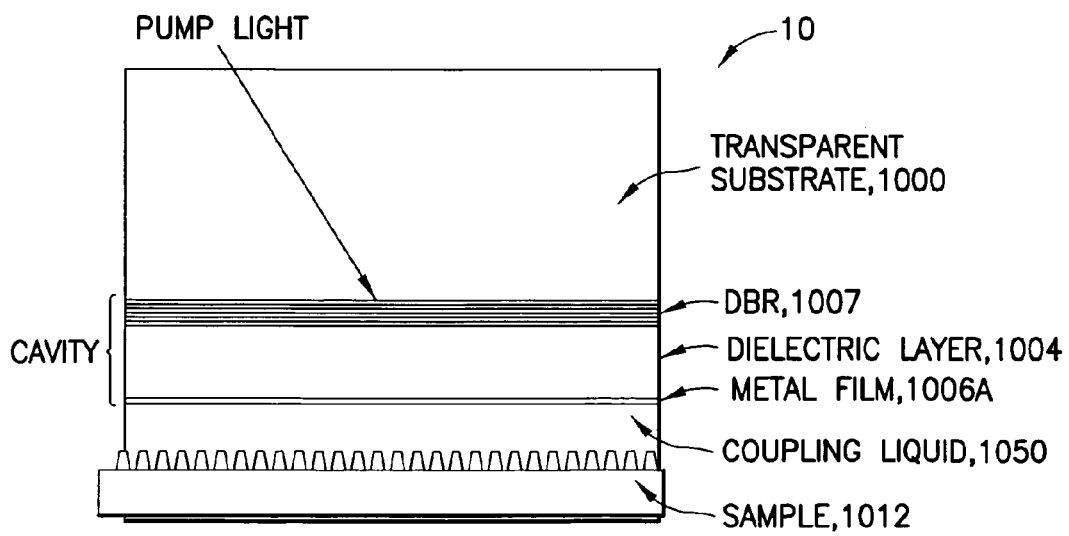
Figure 13:
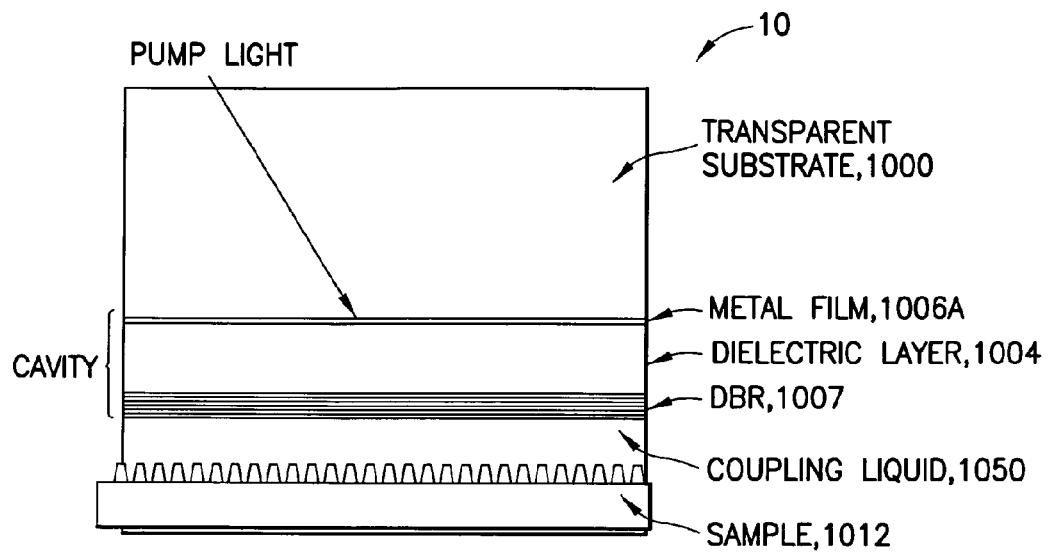

In accordance with another exemplary embodiment of the invention, there is provided as shown in FIGS. 12 and 13 an optical cavity in which there is one metal film 1006A (which may be Al), the dielectric layer 1004, and a dielectric Bragg mirror or reflector (DBR) 1007. Again, the relation between the wavelength of the light and the width of the dielectric layer 1004 is such that a standing optical wave is set up inside the cavity. Compared to the embodiment shown in FIG. 11, the embodiments of FIGS. 12 and 13 have the advantage that light is absorbed in only one part of the structure. As a consequence, a single sound pulse is generated instead of the double pulse produced in FIG. 11. In designing a structure of this type it is advantageous to choose the materials and layer thicknesses so that acoustic reflections are as small as possible. This is so that the sound pulse, or pulses, that are generated by the pump light do not undergo reflection within the structure, thereby producing additional sound pulses that would make the analysis more complicated. Thus, for example, it is preferable for each of the materials used in the DBR 1007 to have approximately the same acoustic impedance, where the acoustic impedance Z is defined as the product of the mass density and the sound velocity.

Figure 14:
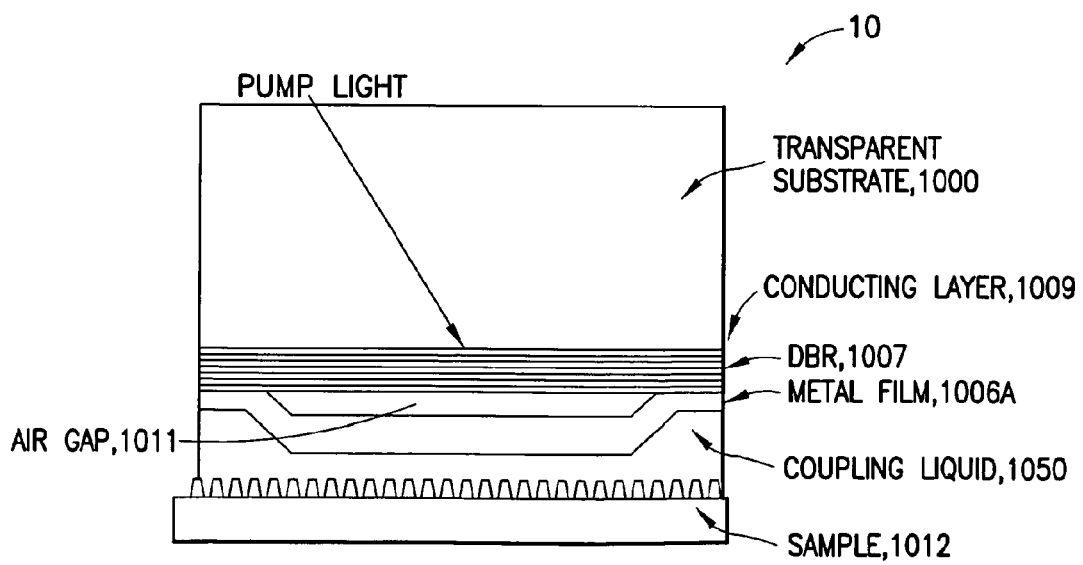

FIG. 14 shows a further embodiment of the opto-acoustic transducer assembly 10 having an ability to tune the optical cavity. For example, one of the reflecting elements in the cavity is fabricated as a thin membrane (metal film 1006A in this non-limiting example) supported from its edges so that the cavity includes an air gap 1011. The space between the two reflectors (the metal film 1006A and a DBR 1007 in this non-limiting example) may be just the air gap 1011, or it could be the air gap 1011 in addition to the dielectric layer 1004 (not shown). The air gap 1011 may be tuned electrostatically to give optimal characteristics for the pump light. Reference with regard to fabrication of a MEMS-tunable cavity for a vertical cavity surface emitting laser (VCSEL) can be made to Connie Chang-Hasnain, "Micromechanical Tunable Vertical Cavity Lasers," Chapter in Vertical-Cavity Surface-Emitting Lasers: Technology and Applications, pp 279-316, ed. J. Cheng and N. Dutta, Gordon Breach Science Publishers, 2000. The MEMS approach is herein applied specifically to the opto-acoustic transducer assembly 10. Note that with regard to the air gap 1011 only the sound that is generated in the reflector 1006A that is in contact with the coupling liquid 1050 will enter the liquid and reach the sample 1012. Thus, it is preferred that this reflector be made of a material that absorbs some of the pump light, whereas the other reflector can be a metal, a semiconductor, or the DBR 1007 (in which substantially no light is absorbed). Since a negligible amount of heat passes across an air gap, and the thermal conductivity of most liquids is low, the heat that is deposited by the pump pulse in the reflector 1006A that is in contact with the coupling liquid 1050 may be conducted away by a flow in the lateral direction. Thus, it may be preferred that the reflector 1006A be made of a material of high thermal conductivity and have a sufficient thickness in order that its temperature rise is not excessive.

In the embodiment shown in FIG. 14 a transparent conducting film or layer 1009, such as InO, is deposited onto the substrate 1000. When a voltage difference is applied between the conducting layer 1009 and the metal film 1006A a force is exerted on the metal film 1006A and the spacing of the cavity is changed by a change in the size of the air gap 1011, thereby tuning the optical characteristics of the cavity.

Note that it also possible to change the tuning of the cavity by other means. As non-limiting examples:

a) The thickness of the dielectric layer 1004 and the dielectric constant of this layer can be changed by a change in temperature.

b) If a piezoelectric material is used for the substrate 1000 then application of an electric field results in a strain in the substrate 1000, which in turn results in a strain in the dielectric layer 1004 of the cavity. This strain produces a change in thickness of the dielectric layer 1004 and a change in dielectric constant.

c) If the dielectric layer 1004 is made from a material that lacks a center of symmetry, a linear change in the dielectric constant can be produced by application of an electric field (Pockels effect). For example, films of zinc oxide may be prepared that lack a center of symmetry.

It should be appreciated that other techniques to tune the resonant cavity may be applied. For example, one approach may be based on a whispering gallery structure. Consider in this regard a circular plate dielectric optical structure where modes run around the edges of the plate. In this case a metal transducer film can be placed at the center of the disk, with a diameter selected to have a finite coupling to the whispering gallery modes (without significantly impairing the Q) while defining the effective diameter of the acoustic beam launched from and received by the transducer 10.

Further in regard to this embodiment, whispering gallery resonators (WGR) are compact guided wave optical device structures which enable high-Q resonators to be implemented at near infrared and visible wavelengths. Optical ring resonators (ORR) are related structures where likewise, light waves are confined in periodic orbits within low loss optical media. Due to the resonant cavity nature of these wave orbits, the optical confinement is effective only at very specific light wavelengths—hence the structures distinctly possess resonator modes with narrow linewidth. The WGRs and ORRs have been used in the past as the basis of semiconductor lasers (see, for example, "Blue-Green Laser Emission from ZnSe Quantum Well Microresonators", M. Hovinen, J. Ding, A. V. Nurmikko, D. C. Grillo, Y. Fan. J. Han, H. Li, and R. L. Gunshor, Appl. Phys. Lett. 63, 3128 (1993)), and have been proposed as sensors, including bio-sensors and thermal sensors. Reference in this regard can be made to, for example, U.S. Pat. No. 6,781,696, "Apparatus and Method for a Microsphere Whispering-Gallery Mode Evanescent-Wave Sensor", Rosenberger et al.; Vollmer, F., D. Braun, A. Libchaber, M. Khoshsima, I. Teraoka, S. Arnold, 'Protein detection by optical shift of a resonant microcavity', Appl. Phys. Lett. 80, 4057-4059 (2002); and G. Guan, S. Arnold, and V. Otugen, "Temperature measurements using a microoptical sensor based on whispering gallery modes," AIAA J. 44, 2385-2389 (2006).

Figure 22A:
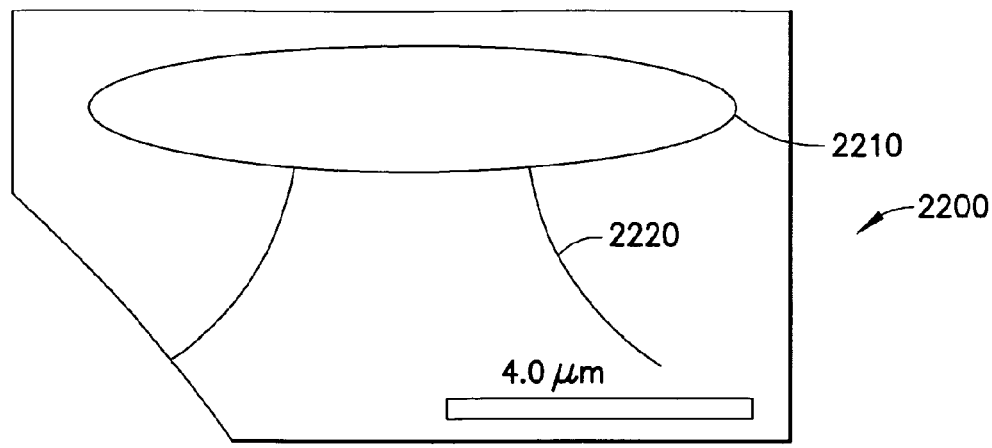
FIGS. 22A and 22B illustrate an electron microscope image of a planar whispering gallery resonator (WGR) that is composed of a circular optical dielectric disk supported by a central pedestal, and a top-view of a, optical ring resonator (ORR) that is composed of input/output ridge waveguides and a high-Q ring microresonator, respectively.
Figure 22B:
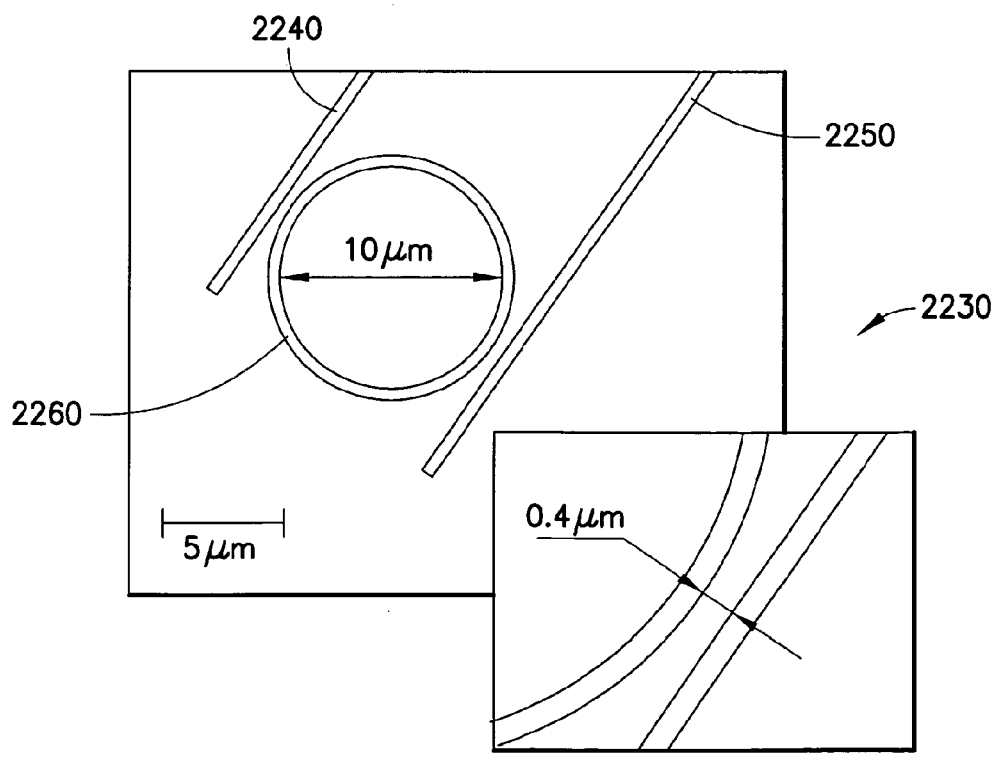

FIGS. 22A and 22B illustrate the generic structure of typical planar optical WGR 2200 and ORR 2230 devices, respectively. These particular examples were fabricated for specific optoelectronic device applications. The WGR 2200 of FIG. 22A is composed of a circular optical dielectric disk 2210 supported by a central pedestal 2220. The ORR 2230 of FIG. 22B. is composed of input/output ridge waveguides 2240, 2250 and a high-Q ring microresonator 2260. Exemplary and non-limiting dimensions are shown in FIGS. 22A and 22B, including in the enlarged portion of FIG. 22B that depicts an exemplary spacing between the ridge waveguide 2250 and the ring microresonator 2260. In each case, light is coupled to the structures by optical fibers or other auxiliary guided wave structures which are placed within the evanescent wave reach of the microresonator. In addition to the planar version, the WGR 2200 and ORR 2230 can also be implemented in spherical or ellipsoidal, or in a prism-like 3D geometry.

The utility of the WGR 2200 and ORR 2230 as sensors in general is due to the fact that the spectral position of the guided light modes, i.e., the singular wavelengths at which the resonator is functional, is sensitively determined by the geometrical dimensions and the index of refraction of the whispering gallery or ring resonator materials, making these structures very sensitive to small variations in either or both properties. Depending on optical losses of the constituent materials, Q-factors can be achieved ranging from a few thousand to in excess of a million.

Since the optoacoustic sensor is a device where sound waves affect either the index of refraction or the displacement of a material surface/interface, the above mentioned high-Q resonator structures may be beneficially used, in accordance with the exemplary embodiments of this invention, for the detection of high frequency ultrasound. When WGR 2200 and ORR 2230 devices are fabricated from dielectric, semiconductor materials, including thin film metal coatings, an incoming pulsed laser light that is coupled into the device can detect the arrival of ultrasound in the device structures. The changes in the index of refraction and/or surface displacement associated with the arriving sound pulse are detected as modulation of the reflected incident light pulses from the structure, due to shifts in the resonance frequency of the confined optical modes. At the same time, the same structure can be employed to initially launch a strain pulse in the device by separate optical excitation pulses which is transmitted to the target material.

With regard to a further embodiment of this invention, it is noted that sound can also be generated efficiently using certain heterostructures composed of certain Group III-V alloys, such as GaN/InGaN or AlGaN/GaN thin film heterostructures. These structures exhibit very large piezo-effects, and when a light pulse excites carriers by inter-band optical absorption a large stress is generated that in turn launches a high amplitude sound pulse. A specific implementation has been described in the paper E. Makarona. B. C. Daly, J.-S. Im, H. J. Marts, A. V. Nurmikko and J. Han, "Coherent Generation of 100 GHz Acoustic Phonons by Dynamic Screening of Piezoelectric Fields in AlGaN/GaN Multilayers", Appl. Phys. Lett. 81, 2791 (2002). While originally disclosed in the context of the Fresnel lens this type of transducer assembly may also be used for the non-focusing opto-acoustic transducer assembly 10.

Further with regard to techniques to fabricate acoustic lenses, there are several exemplary (and non-limiting) methods that can be employed:

a) The concave surface of the lens, such as those shown herein in FIGS. 1A and 1B, may be fabricated in a polymeric material by using a silica sphere as a mold, and then etching out the sphere.

b) The concave surface of the lens may be fabricated by preparing a film of suitable material, and then using a nanoindentor to form a cavity in the surface of the film. In this embodiment the film is prepared from a material that will undergo plastic flow, and the tip of the nanoindentor is provided with a shape that produces a cavity of the desired geometry.

c) The concave surface may be produced by electron beam grey scale lithography and dry etching.

d). The concave surface may be produced by first depositing a layer of photoresist onto the surface, forming a small hole in the photoresist, and then using wet etching through the hole to form a spherical cavity.

In all of the various embodiments discussed thus far it may be advantageous to incorporate additional films into the structure. For example, if an optical cavity of the type shown in FIG. 11 or 12 is used, an additional film may be deposited between the aluminum film 1006 and the coupling liquid 1050. Such an additional film may be used to, as non-limiting examples: a) protect the aluminum film 1006 from oxidation when exposed to air; and/or b) to enhance the transmission of sound into the coupling liquid 1050. In order to enhance the sound transmission, the additional film is preferably composed of a material having acoustic properties that are appropriately related to those of the transducer film, or films, and those of the coupling liquid 1050.

Figure 15:
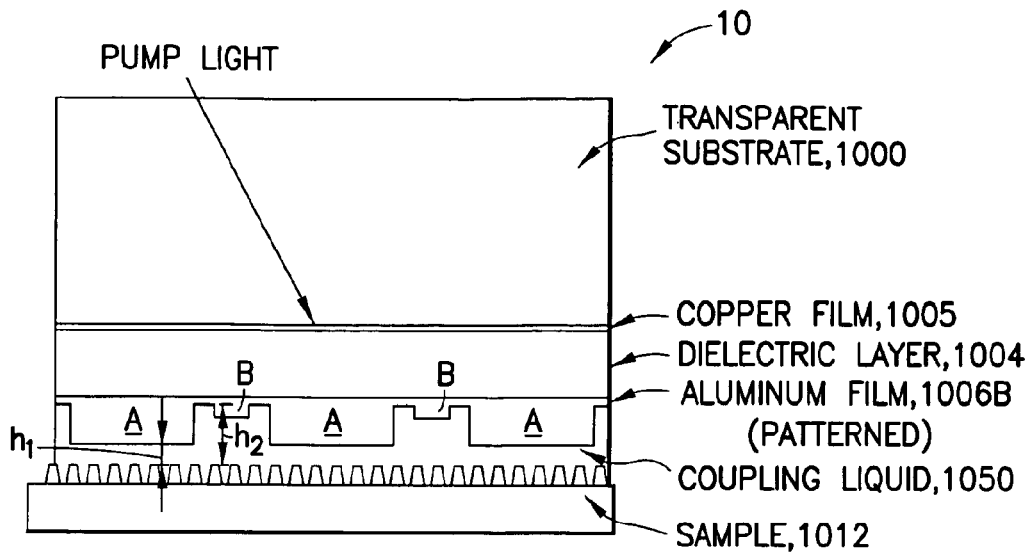
Figure 16:
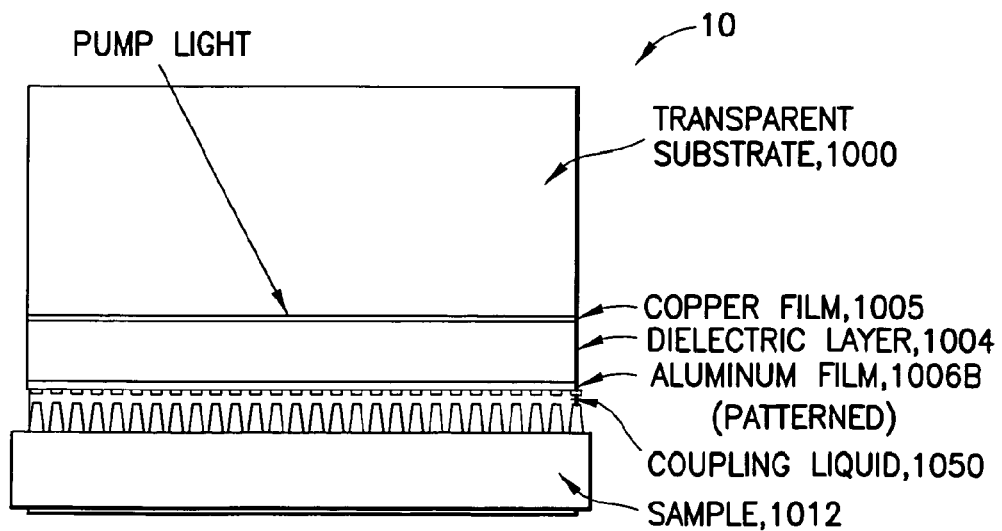
Figure 15A:
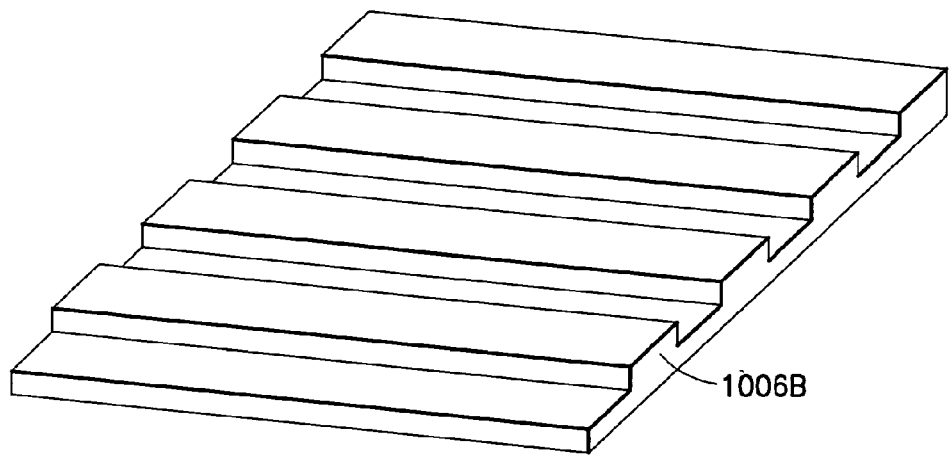
FIGS. 15A and 15B are two enlarged elevation views showing different patterning structures.
Figure 15B:
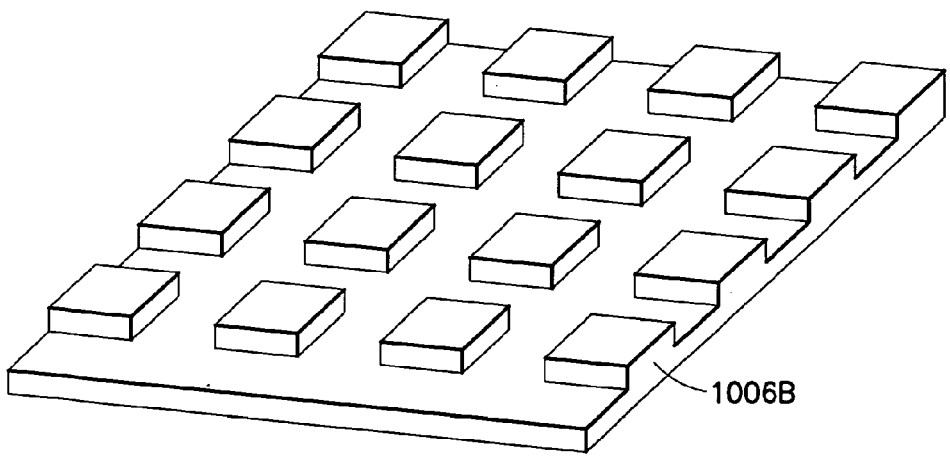

For some applications advantages may be gained by using an optical cavity, or other sound transducer, that is laterally patterned. Two non-limiting examples are shown in FIGS. 15 and 16. Here the lower surface of the metal (e.g., aluminum) film 1006B is patterned (i.e., it exhibits a three dimensional structure). As a result, and instead of a simple plane sound wave being launched through the coupling liquid 1050 toward the sample 1012, a more complicated disturbance is created. For example, the wave that is launched towards the sample 1012 surface exhibits an amplitude that varies with lateral position, and sound waves are launched that propagate in directions other than normal to the surface of the film 1006B. Non-limiting examples include the following.

a) The film 1006B may be patterned as in FIG. 15. With this type of transducer the distance of one part of the film 1006B (part A, shown as $h_1$) above the surface of the sample 1012 is different from the distance of another part of the surface (part B, shown as $h_2$). If the linear dimensions of both the areas A and B are larger than the heights $h_1$ and $h_2$ from the surface of the sample 1012, and also larger than the repeat distance of the pattern on the surface of the sample 1012, one may consider that the measured signal is approximately the sum of the signals that would be obtained with unpatterned transducers at heights $h_1$ and $h_2$. Thus, the use of a transducer 10 of this type can provide a means to extract information that, if an unpatterned sample were used, would require two measurements with different heights of the transducer from the sample. The areas comprising regions A and B may be patterned as arrays of strips running across the surface, as shown in FIG. 15a (one dimensional patterning), or the area making up regions A could consist of rectangular structures with regions B comprising the remainder of the surface of the aluminum film 1006, as shown in FIG. 15b.

b) The transducer film 1006B may also be patterned with a repeat distance that is the same or about the same as the repeat distance of the features of the surface of the sample 1012, as shown in FIG. 16. In this embodiment the measured signal is highly dependent on the lateral position of the transducer 10 with respect to the sample 1012, i.e., if the raised areas on the transducer film 1006B match the raised areas of the surface of the sample 1012 (the condition shown in FIG. 16) the measured signal from the transducer 10 signal will be different from when the raised areas on the transducer film 1006B match the intervening low area of the surface of the sample 1012. Thus, measurements with this type of transducer 10 may be used to make a precise determination of the lateral position of the features appearing on the surface of the sample 1012.

This latter embodiment may be particularly useful when it is desired to precisely register the surface of the sample 1012 during a process, such as a patterning process used during the manufacture of integrated circuits. In this case an overlay problem is solved as currently it may be necessary to position and reposition a semiconductor wafer with a resolution of less than 10 nm between process steps. In this application a current (expected) pattern on a portion of the surface of the wafer can be duplicated on the lower surface of the transducer 10, which then functions as a pattern sensor to enable the alignment to occur when positioned over the corresponding portion of the wafer surface. Alternatively, the wafer surface can be provided with a predetermined alignment pattern that is also duplicated on the lower surface of the transducer 10.

Note that the pattern features on the transducer 10 can be provided to accommodate more than just step heights $h_1$ and $h_2$.

Described now are number of enhancements and extensions to the exemplary embodiments of the invention that have been described thus far.

Figure 23A:
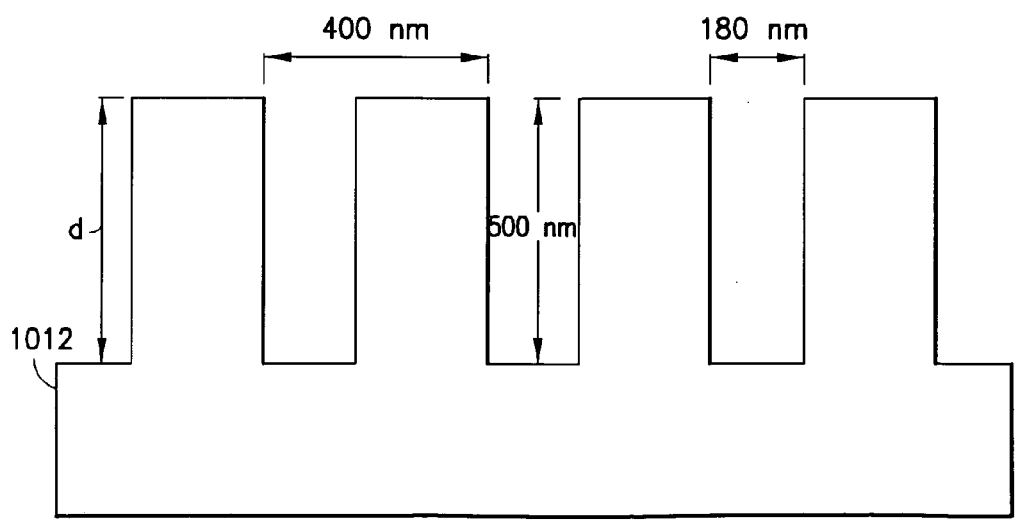
FIG. 23A is an enlarged cross-sectional view of a particular sample having a plurality of trenches.
Figure 23B:
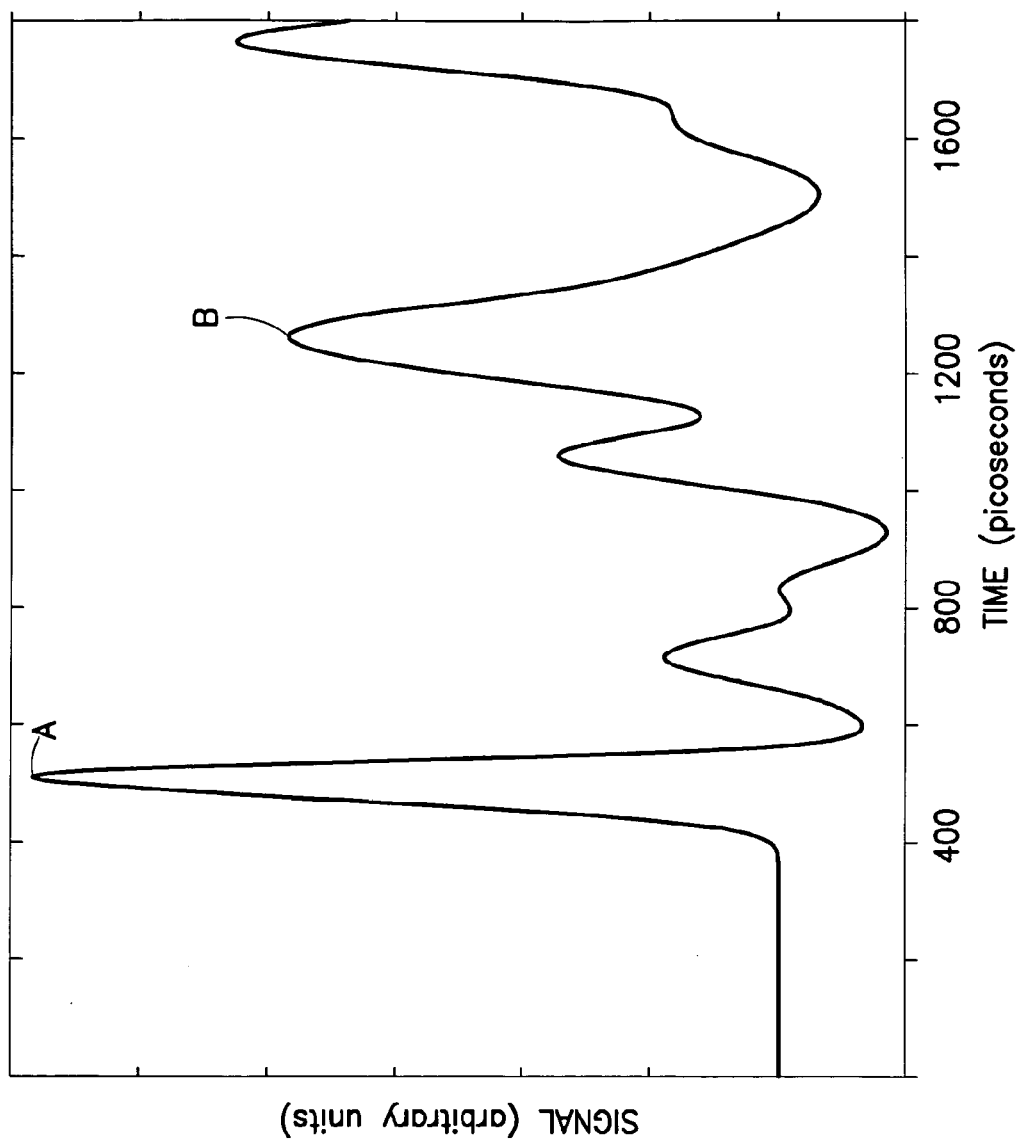
FIG. 23B shows the corresponding output response of the acousto-optic transducer.

One method to determine certain properties of the sample 1012 is based on the analysis of specific features evident in the output of the acousto-optic transducer (AOTA) 10, such as in any of the embodiments of the acousto-optic transducer 10 described above. Consider for example the type of sample 1012 shown in FIG. 23A. The sample 1012 in this case is characterized by a series of trenches of depth h with dimensions as shown. The sample material may be silicon dioxide and the coupling fluid or medium 1050 is water. The AOTA 10 (not shown) may be located at a height of 400 nm above the uppermost surface of the sample 1012. The results of a computer simulation of the output of the AOTA 10 are shown in FIG. 23B. The echo A arises from the part of the generated strain pulse that has been reflected at the top of the sample 1012. The echo B arises from the part of the strain pulse that propagates down to the bottom of the trenches and is reflected there. The depth d of the trench can be determined simply from the difference between the arrival times $T_A$ and $T_B$ of the two echoes A and B, i.e., $$d = \frac{T_B - T_A}{2} c \qquad (1)$$

where c is the speed of sound in water (the assumed coupling medium in this example).

Figure 24:
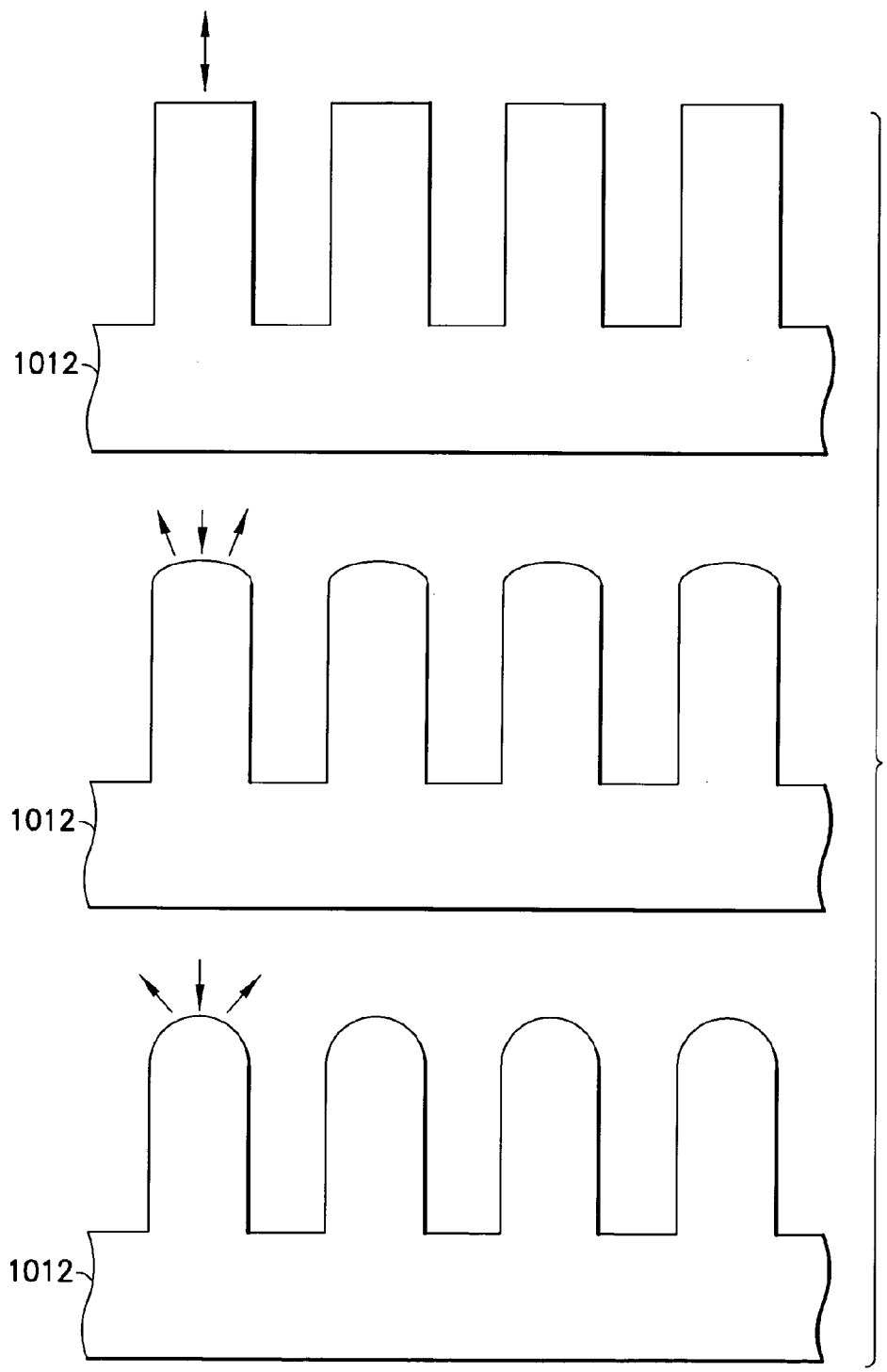
FIG. 24 shows an enlarged cross-sectional view of three samples that differ in the radius of curvature of a top-most portion, and is useful in explaining a method to characterize the samples based on a best-fit to a plurality of simulated output responses of the acousto-optic transducer.

As a second example of the use of specific features of the signal to determine properties of the sample, consider the three sample types shown in FIG. 24. The only difference between these three samples is the curvature of the surface at the top of the sample structure. If this portion of the surface is flat, as in the top-most sample, the sound reflected from it produces a strong echo at the AOTA 10, and as the curvature increases the reflected sound will not all return directly to the AOTA 10, but is instead reflected with a range of directions giving a weaker echo. Thus, for a series of samples 1012 that have identical geometry, except for the curvature of the top surface, the amplitude of the echo from this surface can be used to deduce the curvature of this surface.

Another method of analysis of samples uses computer simulations of the output from the acousto-optic transducer assembly 10, such as was discussed above with respect to FIG. 7. Reference in regards to the following discussion can be made to FIG. 25, which is similar to the system shown in FIG. 7, and which further shows a simulation results library (library) 2015. The simulation results library 2015 may be embodied as a database of simulation results. The computer simulation is based on assumed values for, as non-limiting examples, the geometry and elastic properties and mass density of the materials making up the sample 1012. The simulated output can then be compared with the measured output of the AOTA 10. The computer simulation may be repeated for different assumed values of the geometry and elastic properties of the sample 1012 in order to find those values that result in a simulated output that is as close as possible to the measured output. The steps involved in performing the computer simulation may be as described below.

a) The absorption of the pump light in the AOTA 10 is first considered. From the known thickness and material properties of the thin film layers making up the AOTA 10, the energy absorbed in the one or more metal or semiconducting films is determined. This leads to an increase in temperature of these films. The temperature rise within a particular film will, in general, not be uniform throughout the film.

b) As a result of the increase in temperature, a thermal stress is set up in the one or more metal or semiconducting films. This stress can be calculated from the thermal expansion coefficient and elastic properties of these materials.

c) This stress results in the propagation of one or more strain pulses which enter the coupling fluid (medium) 1050 and interact with the sample 1012. For assumed geometry and elastic properties of the sample 1012, the propagation of these pulses can be calculated using, for example, finite element or finite difference methods.

d) When the strain pulses return through the coupling fluid 1050 and reenter the AOTA 10, there is a resulting change in the optical characteristics of the AOTA 10. For example, this is a change in the thickness of one or more of the films composing the AOTA 10, and the strain causes a change in the optical constants of the material of the film(s). The change in the optical reflectivity, or other optical characteristic of interest, of the AOTA 10 may be calculated.

For most solid materials the mass density and sound velocity are substantially larger than the mass density and sound velocity of the coupling mediums that are likely to be of interest. As a result, for some samples it may be sufficient to perform a simplified computer simulation of the output of the AOTA 10 in which an approximation is made that the sample 1012 is rigid.

For many samples of interest, the elastic properties and density of the materials making up the sample 1012 are known quantities. In this situation, it is only the geometry of the sample 1012 that needs to be adjusted to obtain a best fit between the simulated and measured outputs of the AOTO 10.

Figure 20:
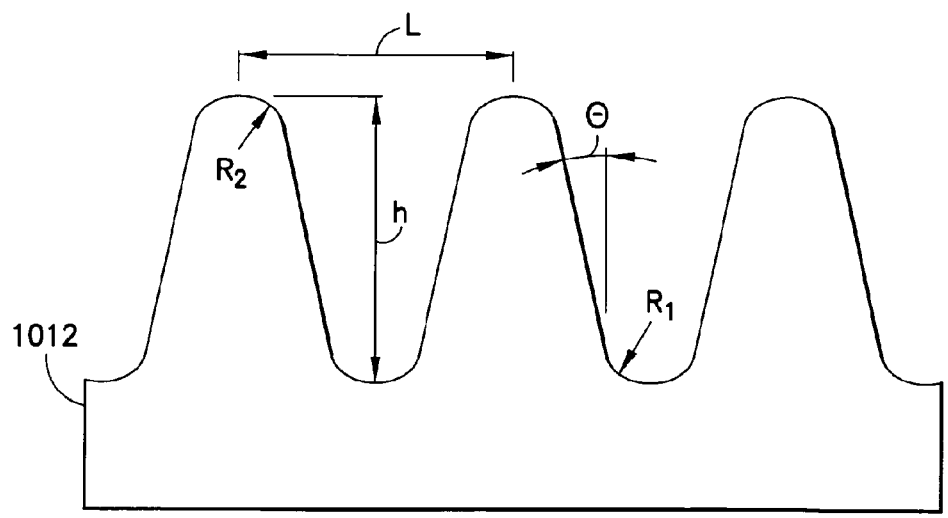

There exist a number of methods that can be used to adjust the assumed properties of the sample 1012 so as to achieve a best fit between the simulated and measured outputs of the AOTA 10. A first example of a method is to prepare the library 2015 of simulated outputs of the AOTA 10 for a large number of assumed geometries, and possibly other properties (e.g., elastic and mass density) of the sample 1012. These simulated outputs give a calculated output $y_{sim}(t_n)$ at a set of N times $t_n$, where n runs from 1 to N. To appreciate the nature of the library 2015, consider as an example the surface profile of a sample as shown in FIG. 20. The profile of this type of sample can be described by means of the following parameters:

a) the depth of trenches h;
b) the repeat distance L;
c) the radius of curvature $R_1$ at the bottom of the trenches; and
d) the radius of curvature $R_2$ of the top of the structure.

Simulations are performed based on a range of values for each of these four parameters. For example, 10 different values of each parameter may be considered, giving in total 10,000 simulated outputs of the AOTA 10. The measured output is then compared with the library 2015 of simulated outputs, and the values of those four parameters that yield a simulated output closest to the measured output is then determined. The term "closest to" as used here may refer to the sum of the squares of the difference between the measured output $y_{meas}(t_n)$ at the times $t_n$ and the simulated output $y_{sim}(t_n)$. Thus the parameters that minimize the quantity:

$$S = \Sigma [y_{meas}(t_n) - y_{sim}(t_n)]^2 \quad (2)$$

are taken to be the best fit parameters that are descriptive of the actual geometry of the sample 1012.

Figure 25:
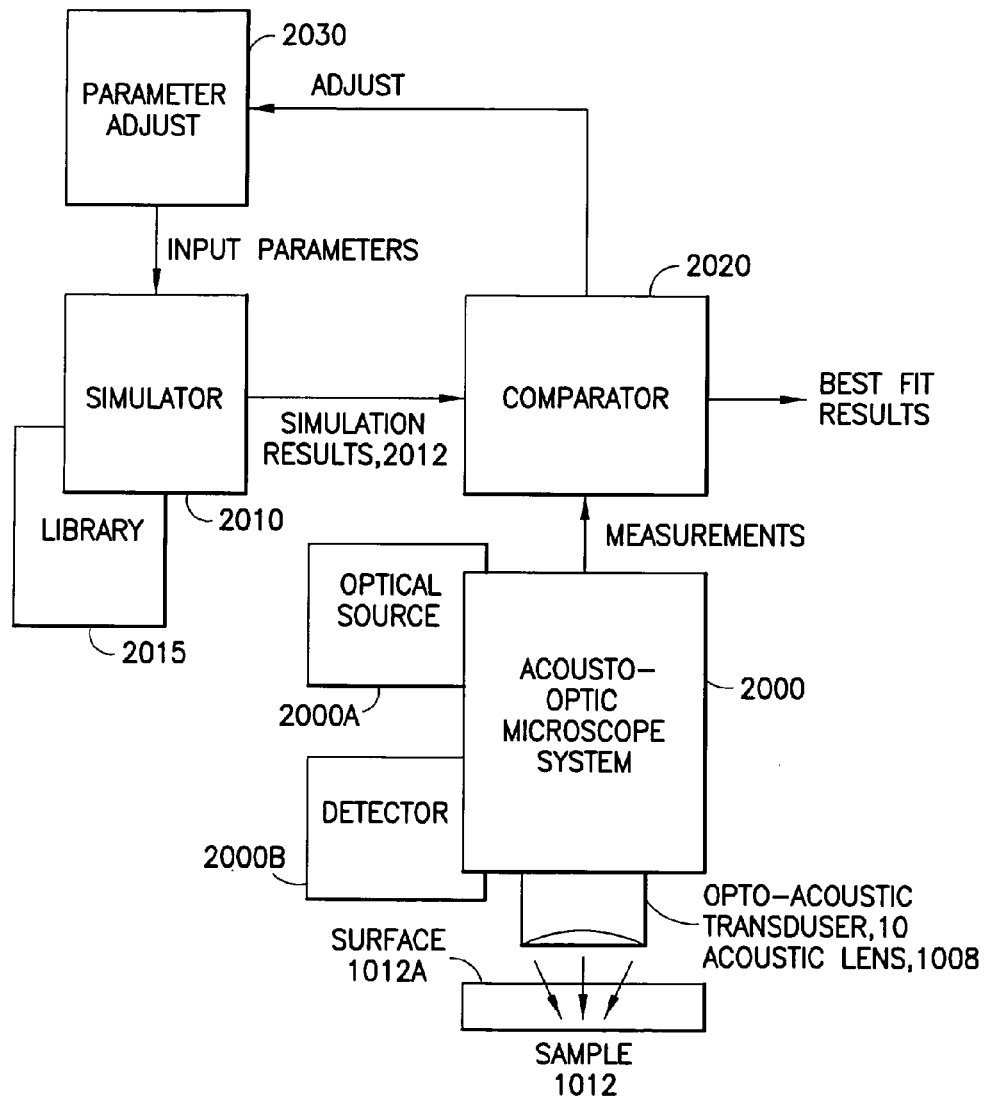
FIG. 25 is similar to the system shown in FIG. 7, and further shows a simulation results library.

In this and certain of the exemplary embodiments considered below it may assumed that the "simulation results" output 2012 of the simulator block 2010 in FIG. 25 is actually an output from the library 2015, which was pre-loaded with (potentially) a large number of simulation result values.

As can be appreciated by those skilled in the art, there are a number of variations of the method that may be advantageously used for certain sample types.

The evaluation of the sum S may be restricted to include only outputs lying in a certain time range where the output was particularly sensitive to whichever of the parameters h, L, $R_1$ or $R_2$ was of greatest interest.

Instead of using the sum as defined by Eq. 2, a weighting function W(t) may be introduced and the sum $$S = \Sigma [y_{meas}(t_n) - y_{sim}(t_n)]^2 W(t_n) \quad (3)$$

may then be used to determine the best fit to the measured data.

While the spatial form of the strain pulse generated by the acousto-optical transducer 10 may be accurately known, there may be an uncertainty in the amplitude of the generated strain pulse. This may lead to uncertainty in the amplitude of $Y_{sim}(t)$, i.e., the simulated output would be $Ay_{sim}(t)$, where the variation of $y_{sim}(t)$ with t was accurately known but A was an unknown scale factor. This situation could occur, for example, if the energy of the pump light pulse used to generate the sound was not known, or if the area of surface of the AOTA 10 that was illuminated by the pump pulse was not known. In this case the function S of Eq. 3 may be replaced by:

$$S = \Sigma [y_{meas}(t_n) - Ay_{sim}(t_n)]^2 W(t_n) \quad (4)$$

where it is implied that the scale factor A is to be adjusted so as to minimize the value of S. This is equivalent to the use of the following expression:

$$S = \frac{S_{mm}S_{ss} - S_{ms}^2}{S_{ss}} \quad (5)$$

where the following quantities have been introduced $$S_{mm} = \Sigma y_{meas}(t_n)^2 W(t_n)$$

$$S_{ms} = \Sigma y_{meas}(t_n) y_{sim}(t_n) W(t_n)$$

$$S_{ss} = \Sigma y_{sim}(t_n)^2 W(t_n) \quad (6)$$

A number of techniques may be used to reduce the amount of time needed for the computer to search through the potentially large number of simulated outputs resident in the library 2015. For example, the simulation results may be presorted according to a particular attribute. Thus, for example, one may presort the set of simulations into a number of groups (with each group labeled by an index i) such that the group i contains those simulations for which the arrival time of the first echo signal from the sample occurs in a certain time range $T_i$ to $T_{i+1}$, where the times $T_i$ form a sequence that increases with the index i. Then, if the measured signal shows a first echo arriving from the sample at time τ one can compare the measured signal only with those simulated signals for which the echo arrival time is in the range close to τ. Thus, one would find the group i for which $T_i < \tau < T_{i+1}$ and then search only the group i to find the simulated output that is closest to the measured output. In this example, the attribute is the arrival time of the first echo signal, but it is within the scope of the exemplary embodiments of this invention to use other attributes that are advantageous for particular samples.

As one non-limiting example, the attribute may be the ratio of the height of a first echo to a second echo. As another non-limiting example, the attribute may be the width of an echo. It is also within the scope of these exemplary embodiments of the invention to use two (or more) attributes to presort the set of simulated data into groups that contain all simulations in which a first attribute lay in a certain range and a second attribute lay in a certain range.

By finding the simulation data that is closest to the measured data, a set of parameters describing the sample surface 1012A giving a best fit between simulation and measurement can be obtained. However, it is important to note that the set of parameters that are obtained in this way are simply the best amongst the sets of parameters which are included in the simulation results library 2015. As an example, consider again the sample 1012 shown in FIG. 20. Assume that the library 2015 contains the results of simulations in which the height parameter h takes on 10 equally-spaced values between 200 nm and 290 nm. If the best fit simulation in the library 2015 is found to be with h=240 nm, the determined value of h is uncertain by an amount that is on the order of 10 nm. To improve this accuracy using the library 2015 method as just described one may require that the spacing of the values of the parameter h be reduced. This can be done in at least two ways, both of which have substantial difficulties. First, one can simply increase the number of values of h included in the library 2015 while keeping the total range of values constant (200 nm to 290 nm in the above example). This has the disadvantage that the number of simulations making up the library 2015 increases, meaning that more time is needed to prepare the library 2015 and also more computer time is needed to search the library 2015 for the best fit. The second approach is to keep the number of values of h constant but to decrease the total range of values of h. For example, this could be reduced to the range 230 nm to 275 nm which would give a spacing between values of h of only 5 nm. This approach has the disadvantage that a sample may be encountered which has a value of h that lies outside of the range of values contained in the library 2015. For this sample a search of the library 2015 would not return the correct value of h. Thus, alternate methods may be used to improve the fitting procedure. Some examples are now given of means to overcome these difficulties. Based at least on these descriptions, other approaches may become apparent to those skilled in the art.

In a first method, a search of the library 2015 is made and the set of parameters that give a best fit between the simulated and measured outputs is found. Let these parameters be $x_{best,k}$ where k=1, . . . K , and K is the total number of parameters (K=4 in the above example). On may consider that these parameters define the location of a best fit point in "parameter space", i.e., the space of the variables $x_k$. This space has K dimensions. One may then construct a function that smoothly interpolates between the value of S at the best fit point in the parameter space and the values of S at some number of neighboring points in parameter space. This approach then locates the position in parameter space at which S has its minimum value, and in this manner obtain a new best set of values for the parameters.

As a highly simplified illustration of this method, consider a situation in which the sample 1012 is described by only one parameter (e.g., the height h). In this example K=1. A search of the library 2015 will find the simulation in the library 2015 that gives the best fit. Let the height for this simulation be $h_0$ and the value of S be $S_0$. Let the value of the height at the next smaller height in the library 2015 be $h_1$ and the value at the next larger height be $h_2$, and let the values of S for these two heights be $S_1$ and $S_2$. For simplicity, assume that the library 2015 has been constructed in such a manner that $h_2-h_0=h_0-h_1=\Delta h$. One may then construct the quadratic function:

$$S(h) = S_0 + (h - h_0)\frac{S_2 - S_1}{2\Delta h} + (h - h_0)^2 \frac{S_2 - 2S_0 + S_1}{2(\Delta h)^2}, \quad (6)$$

which has the property that $S(h_0)=S_0$, $S(h_1)=S_1$, and $S(h_2)=S_2$. The location of the minimum of the function S may then be used as an estimate of the best fit value for h. This gives $$h_{best\ fit} = h_0 - \frac{\Delta h}{2} \frac{S_2 - S_1}{S_2 - 2S_0 + S_1}. \quad (7)$$

A second method begins with the best set of parameters that are found in the library 2015, and then performs new simulations with parameters that are adjusted relative to the original values. The parameters are adjusted so as to find new values such that the sum S is reduced to its minimum value. There are a number of well known algorithms that can be used to achieve this minimization. One such algorithm is the Levenberg-Marquardt method. Reference in this regard may be made to the discussion in Numerical Recipes, by W. H. Press, S. A. Teukolsky, W. T. Vetterling and B. P. Flannery, 2nd edition, Cambridge University Press.

In a third method one may choose to not use the library 2015, but to perform a first simulation based on an a priori estimate of the sample parameters. Then new simulations are performed with parameters that are adjusted relative to the original values. The parameters are adjusted so as to find new values such that the sum S is reduced to its minimum value. There are a number of well known algorithms that can be used to achieve this minimization. One such algorithm is the above-mentioned Levenberg-Marquardt method.

It is important to note that in most applications of interest measurements are made on a sequence of samples that are all similar. The goal is typically to verify that each sample 1012 in the sequence has a geometry that is sufficiently close to the desired geometry. Thus the library 2015 of simulated outputs needs to be calculated only once for a given type of sample 1012. This library 2015 can be created in advance before measurements are made.

In the method described above some non-trivial amount of computer time may be needed in order to calculate the error sum S for each simulation stored in the library 2015. For certain samples it may be advantageous to use a simpler method to determine the sample parameters as follows. In this method, simulations are performed in advance for a range of values of the set of parameters that describe the sample. Then, for each simulated output, some number J of characteristics of the simulated output are stored on the computer. These might include, by example, the time of arrival of the first and second echoes, the amplitude of these or other echoes, etc. These characteristics are then compared with the values of these same J characteristics obtained in the measured output from the AOTA 10. The library 2015 is then searched to find the set of sample parameters that give the best fit for the simulated and the measured J characteristics. When using this method, an interpolation method similar to that already described can be used to improve the accuracy with which the parameters of the sample 2015 are determined.

It should be pointed out that the library 2015 may include only the results of simulations, or it may include the results of simulations and the results of measurements made on one or more reference samples, or in some embodiments it may include only the results of measurements made on one or more reference samples.

Figure 17:
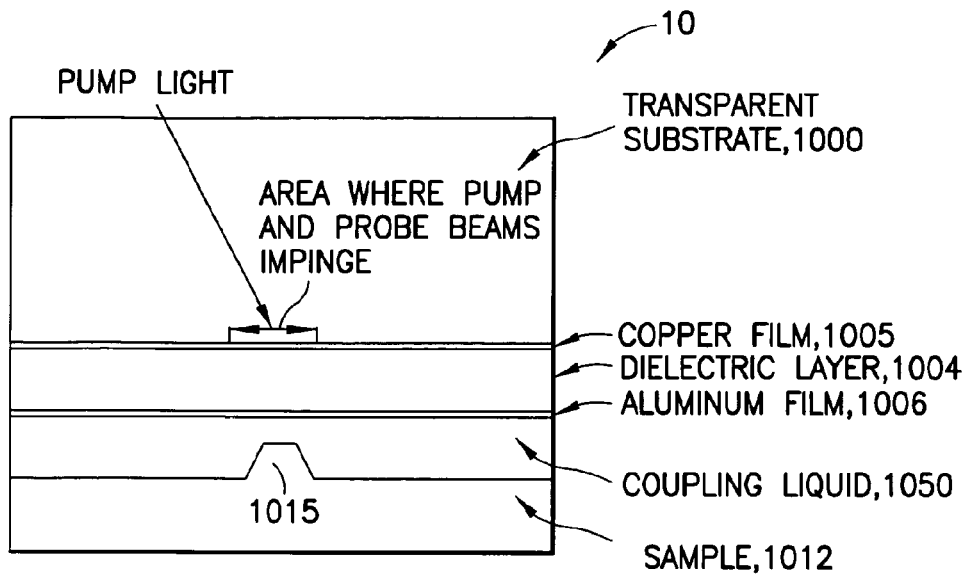

A number of applications of interest of the non-focusing transducer 10 involve measuring samples 1012 that have an array of repeating features, such as would be found in a typical integrated circuit. In these applications the linear dimensions of the area of the transducer 10 that is excited by the pump and probe light pulses is significantly larger than the repeat distance of the sample features. However, it is also possible to use the non-focusing transducer 10 to make measurements on samples that have a single feature that is of interest, such as the feature 1015 shown in FIG. 17. In this case the pump and probe beams are directed to a small area of the optical cavity of the transducer that is located directly above the feature of interest 1015.

Figure 18:
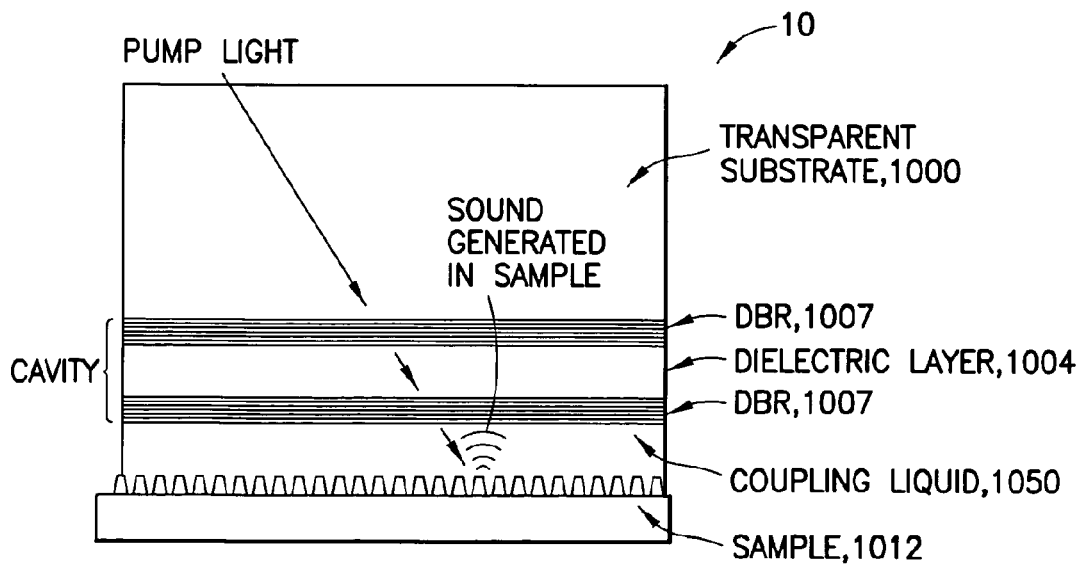

For samples that are opaque over some range of light wavelength, the arrangement shown in FIG. 18 could be used. The optical cavity is formed by two DBR 1007 together with the dielectric layer 1004. The cavity is designed so that there is substantial transmission of the pump light, and the pump light pulses are absorbed in the sample 1012. Sound is generated in the sample 1012 and propagates through the coupling liquid 1050 and into the optical cavity. The cavity is designed so that when the sound pulse enters into the dielectric layer 1004 and the thickness of this layer changes, there is a change in the reflectivity of the probe light pulse. This embodiment employs different wavelengths for the pump and probe light pulses. For many materials the absorption of light is stronger at short wavelengths and, as a result, it may be preferable to have the pump light of short wavelength and the probe light of longer wavelength.

In the previous applications and in the above discussion of the optical cavity/transducer, reference has been made to embodiments that include two mirrors (DBR or metallic) on either side of the dielectric layer 1004. However, it should be noted that the exemplary embodiments extend as well to a broader class of designs that include any multilayer structure having the property that there is a detectable change in optical reflectivity when a sound pulse is incident, and which includes at least one layer that is optically absorbing wherein sound (acoustic energy) is generated. Note that when the optical cavity incorporates a DBR 1007, it is arbitrary to draw a distinction between the dielectric layers that form the DBR 1007 per se and the layer (dielectric layer 1007) that is considered to form a part of the optical cavity. For example, the layer 1007 may be made of the same material as is used for one or more of the dielectric layers that comprise the DBR 1007. Thus, it should be appreciated that the exemplary embodiments of this invention pertain as well to a transducer structure that includes: a) at least one metal or semiconducting film in which a part of the pump light pulse is absorbed, and b) at least one dielectric film, where the thickness and optical properties of the films are selected so that a returning sound pulse results in a measurable change in the optical reflectivity and/or some other optical characteristic of the transducer structure.

Figure 19:
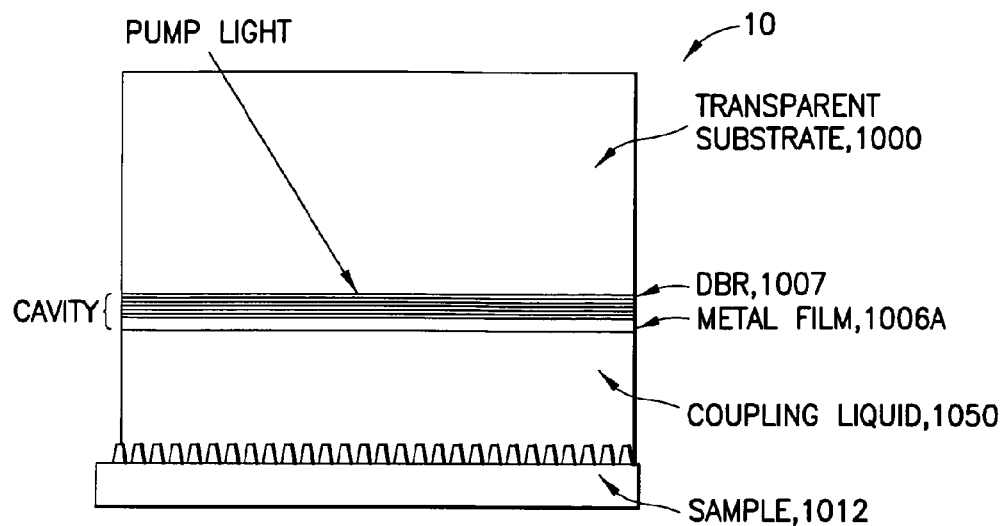

One example of this type of transducer assembly 10 is shown in FIG. 19, where a DBR 1007 is in contact with a metal film 1006A. The DBR 1007 may be designed so that the transmission through it is approximately 50%, and very sensitive to the thickness of the constituent layers of the DBR 1007. Sound is generated when pump light is absorbed in the metal film 1006B. The returning sound passes through the metal film 1006B and enters the DBR 1007. The resulting change in the layer spacing in the DBR gives a large change in the reflectivity to the probe light pulse. Note that the bottom surface of the metal film 1006A may be flat and featureless, or it may be patterned as in the examples shown in FIGS. 15, 15a, 15b and 16.

It should be noted that the exemplary embodiments of this invention are not limited only to the use of the probe pulse for making a measurement of the change in reflectivity. The measured quantity may instead be the change in the reflection coefficient, transmission coefficient, phase of the reflected or transmitted light, polarization of the transmitted or reflected light, or a change in the ellipsometric parameters. One or more of these quantities may be measured to obtain information concerning the surface 1012A of the sample 1012.

It is further within the scope of the exemplary embodiments of this invention to detect the sound returning after propagating through the coupling fluid 1050 through the use of a quantum well structure. One suitable (and non-limiting) type of quantum well structure is described in "Ultrafast Band-Gap Shift Induced by a Strain Pulse in Semiconductor Heterostructures", A. V. Akimov, A. V. Scherbakov, D. R. Yakovlev, C. T. Foxon and M. Bayer, Physical Review Letters, 97, 037401 (2006).

It is further within the scope of the exemplary embodiments of this invention to use separate lasers for the pump and for the probe that run with different repetition rates. This approach may be referred to as asynchronous optical sampling (ASOPS), see, P. A. Elzinga, F. E. Lytle, Y. Jian, G. B. King and N. M Laurendeau, Applied Optics 26, 4303 (1987), "Femtosecond time-resolved optical pump-probe spectroscopy at kilohertz scan rates over nanosecond time delays without mechanical delay line", A. Bartels, F. Hudert, C. Janke, T. Dekorsy, and K. Kohler, Applied Physics Letters 88, 041117 (2006), and the website http://www.gigaoptics.comitwin.html.

In the above description each pump pulse applies acoustic energy to the same area of the sample 1012 with an intensity that varies smoothly across the area. It is also within the scope of this invention to make measurements of the transient optical response by means of an induced transient grating method (see: D. W. Phillion, D. J. Kuizenga, and A. E. Siegman, Appl. Phys. Lett. 27, 85 (1975)). To induce a transient grating each pump pulse is divided into two or more components by means of a beam splitter or beam splitters, these components then pass through separate optical paths, and are then all directed onto the same area of a surface of the transducer assembly 10. If the different components are directed onto the surface with different angles there will be locations within the area where the different components interfere constructively, and locations where the interference is destructive. As a result the total intensity of the pump light will vary across the surface. In the case that only two components are present, the intensity will vary periodically across the surface. The periodicity of the intensity, i.e. the spacing between successive points of maximum intensity, is determined by the wavelength of the pump light and the angles at which the different components of the pump light are incident onto the surface. As a result of this periodic variation in the intensity, the amount of pump light absorbed will vary periodically across the surface of the transducer 10. The amplitude of the sound pulses will therefore vary periodically across the surface of the sample 1012. Consequently, the transient changes in the optical properties of the transducer 10 which result from the returning sound pulses will also vary periodically. This variation of the transient changes in the optical properties of the transducer 10 is equivalent to the production of a transient diffraction grating coinciding with the location of the transducer. Hence, when the probe light is incident on the transducer, a part of the probe light will be diffracted, i.e., a part of the probe light will be reflected in a direction, or directions, away from the direction of specular reflection. Measurement of the intensity of this diffracted probe light as a function of the time delay t between the application of the pump and probe beams provides an alternate method for the characterization of the sound pulses returning from the sample.

As was noted above with respect to the description of FIG. 7 and FIG. 25, the measured response from the sample 1012 may be compared with the results of computer simulations of the expected response, and the parameters assumed for the sample properties adjusted so as to achieve a best fit between the measured response and the simulated response. Sample properties here include the geometry of the sample 1012 including the roughness of the sample surfaces, elastic properties and density. Simulations may be performed using, as non-limiting examples, finite element or finite difference methods. A most complete simulation may include: a) calculation of the light field in the transducer structure 10 when the pump light is incident, b) calculation of the energy absorbed in the different components of the transducer structure 10, c) calculation of the stress that results within the transducer structure 10, d) calculation of the propagation of the sound pulse through the transducer 10, the coupling liquid 1050 and the sample 1012, and e) calculation of the change in the reflection, or other optical property, of the transducer 10 as a result of the returning sound. The calculation preferably includes the sound generated by that part of the pump light that reaches the sample 1012 and is absorbed therein. The calculation of the propagation of the sound preferably includes allowance for the shear and bulk viscosity of the coupling fluid 1050, and for the finite elastic compliance of the sample 1012.

For some applications it may be desirable to perform a simplified version of the simulation. For example, it may be acceptable to approximate the sample 1012 as a rigid structure that the sound pulses do not penetrate.

For a sample 1012 having a surface profile characterized by a series of equally spaced trenches, and as was noted above, the geometrical properties of the sample 1012 that maybe be determined include, see FIG. 20:

a) the depth of trenches h;
b) the repeat distance L;
c) the radius of curvature at the bottom of the trenches $R_1$; and
d) the radius of curvature of the top of the trenches $R_2$.

Note that the sidewall angle of the upstanding features $\theta$ can also be determined.

The exemplary embodiments of this invention also encompass the use of a method in which the measured response from the sample 1012 is recorded for more than one distance of the acousto-optic transducer 10 above the sample surface 1012A.

Note further in this regard that the library 2015 may include simulated results that assume-a plurality of different distances of the acousto-optic transducer 10 above the sample surface 1012A.

The exemplary embodiments of this invention also encompass the use of a method in which the measurement system, such as the one shown in FIGS. 7 and/or 25, is combined with another type or types of sample measurement systems, such as those based on ellipsometry, or reflectometry, or x-ray, and where the results from each measurement system are used alone or synergistically together to obtain critical dimension (CD) and other types of measurements related to the sample 1012.

The measurement system that includes the transducer assembly 10 and related optical, mechanical and electrical components may form a stand alone measurement system, or it may be combined with one or more other types of measurement systems, or it may be integrated or embedded into a photolithography or other type of tool associated with some type of process, such as the processing of integrated circuits. Reference in this regard may be had to the discussion above related to FIG. 16, as it can be appreciated that the transducer 10-based measurement system can be integrated into a semiconductor process flow to enable accurate registration of the semiconductor wafer between process steps.

The exemplary embodiments of this invention may be used to advantage during various phases of the processing of semiconductor wafers, such as during the manufacturing of integrated circuits. One particularly useful and non-limiting application is in conjunction with a chemical mechanical polishing (CMP) process.

Further in this regard, it is common among chip makers (integrated circuit manufacturers) to use a so-called 'dual damascene copper' process to fabricate electrical interconnects between different parts of a chip. This is one non-limiting example of a process which may be effectively characterized using a suitable surface topography system. The dual damascene process may be considered to have five parts: (1) an interlayer dielectric (ILD) deposition, in which a layer of dielectric material (such as a polymer, or glass) is deposited onto the surface of a wafer (containing a plurality of individual chips); (2) CMP, in which the dielectric layer is polished so as to create a smooth surface, suitable for precision optical lithography, (3) a combination of lithographic patterning and reactive ion etching steps, in which a complex network is created comprising narrow trenches running parallel to the wafer surface and small vias running from the bottom of the trenches to a lower (previously defined) electrically conducting layer, (4) a combination of metal deposition steps which result in the trenches and vias being over-filled with copper, and (5) a final CMP step in which the excess copper is removed, leaving a network of copper filled trenches (and possibly vias) surrounded by dielectric material.

Typically the thickness of the copper in the trench areas (i.e., the trench depth), and the thickness of the surrounding dielectric lie in a range of 0.2 to 0.5 microns. The width of the resulting trenches may be in a range of from 100 to 100,000 nanometers, and the copper regions within each chip may in some regions form regular patterns such as arrays of parallel lines, and in others they may have no apparent pattern. Likewise, within some regions the surface may be densely covered with copper regions, and in other regions, the copper regions may be sparse. It is important to appreciate that the polishing rate, and therefore the remaining copper (and dielectric) thickness after polishing, depends strongly and in a complex manner on the polishing conditions (such as the pad pressure and polishing slurry composition), as well as on the local detailed arrangement (i.e., orientation, proximity and shape) of copper and surrounding dielectric regions.

This 'position dependent polishing rate' is known to give rise to variable surface topography on many lateral length scales. For example, it may mean that chips located closer to the edge of a wafer on aggregate are polished more rapidly than those located close to the center, creating copper regions which are thinner than desired near the edges, and thicker than desired at the center. This is an example of a 'wafer-scale' process nonuniformity, i.e., one occurring on a length scale comparable to the wafer diameter. It is also known that regions which have a high density of copper trenches polish at a higher rate than nearby regions with low copper line densities. This leads to a phenomenon known as 'CMP induced erosion' in the high copper density regions. This is an example of a 'chip-scale' process non-uniformity, i.e., one occurring on a length scale comparable to (and sometimes much less than) the linear dimensions of a single chip. Another type of chip-scale nonuniformity, known as 'dishing', occurs within single copper filled trench regions (which tend to polish at a higher rate than the surrounding dielectric material). For trenches greater than a few microns in width dishing may become severe with the result that affected lines later exhibit excessive electrical resistance, leading to a chip failure.

CMP induced wafer-scale and chip-scale process nonuniformities are inherently difficult to predict, and they are subject to change over time as conditions within the CMP processing system evolve. To effectively monitor, and suitably adjust the process conditions for the purpose of ensuring that any nonuniformities remain within acceptable limits, it is important for process engineers to make frequent non-contact surface topography measurements on chips at a large number and wide variety of locations.

The use of the exemplary embodiments of this invention is thus particularly well-suited for detecting a presence of one or both of wafer-scale and chip-scale process nonuniformities that result from the use of CMP.

The use of the exemplary embodiments of this invention beneficially enable the detection and characterization of surface features that are not resolvable by the use of optical techniques, such as dimensions less than, for example, about 50 nm, i.e., dimensions associated with current and future generations of semiconductor wafer processing.

Note that the transducer assembly 10 and related optical, mechanical and electrical components may be used to characterize, for example, metal and other types of lines appearing on an integrated circuit substrate, such as those used to make connections between passive and active devices. However, other types of current and future interconnect elements may also be resolvable, such as lines composed of aligned carbon nanotubes which may have diameters in the sub-10 nm range.

In the exemplary embodiments of this invention the transparent substrate 1000 may be composed of diamond, as diamond exhibits a high thermal conductivity to quickly enable heat generated in the transducer assembly 10 to be extracted, thereby minimizing heat-induced changes in dimensions of the optical cavity and other structures.

The coupling medium 1050 may be water as stated, but is not limited to water. For example, a viscous fluid may behave more along the lines of a solid, and at high acoustic frequencies may be less attenuating than water. In general, it is desired to use as thin a layer of the coupling medium 1050 as possible (e.g., about 0.1 to about 1 micron) to reduce attenuation of the launched and returning sound pulses.

Figure 21:
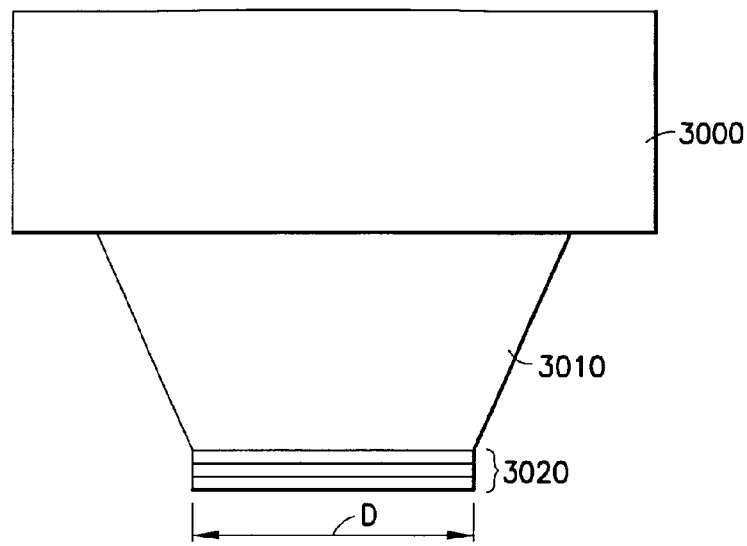
FIG. 21 shows one embodiment of a transducer assembly having a transparent crystalline quartz substrate to which is affixed a tapered transparent substrate composed of diamond on which metal and dielectric layers are deposited to form an optical cavity.

The bottom surface of the transducer 10 may have any suitable dimensions, such as about one centimeter or about 50 microns. For example, FIG. 21 shows one embodiment of the transducer assembly 10 having a transparent crystalline quartz substrate 3000 to which is affixed a tapered transparent substrate 3010 composed of diamond on which metal and dielectric layers 3020 (e.g., aluminum and $SiO_2$) are deposited to form the optical cavity. The diamond substrate 3010 may resemble, or may be, a component usable in a diamond anvil cell. The dimension (D) in this non-limiting example is about 50 microns.

It is also within the scope of the exemplary embodiments of this invention to control the temperature of the coupling medium 1050, and to make measurements of the sample surface 1012A at a plurality of different temperatures. In like manner, the simulation results stored in the library 2015 may include sets of simulation results that assume different temperatures of the coupling medium 1050. The temperature of the coupling medium 1050 may be changed directly, such as by heating or cooling water if water is used as the coupling medium 1050, or indirectly such as by changing the temperature of the sample 1012.

Figure 26:
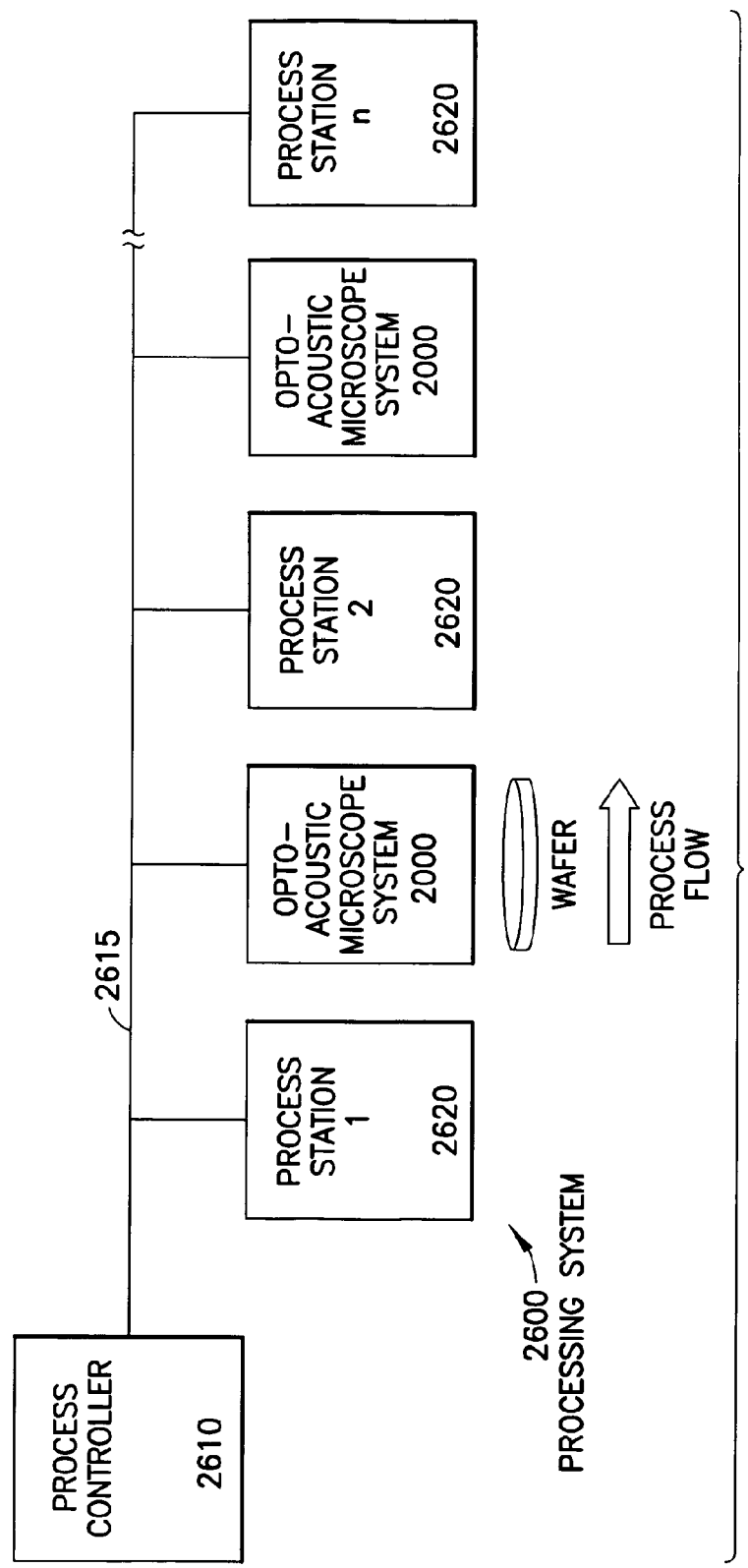
FIG. 26 shows an exemplary embodiment of a processing system 2600 that comprises at least one opto-acoustic microscope system as shown in FIGS. 7 and 25.

FIG. 26 shows an exemplary embodiment of a processing system 2600 that comprises one or more of the opto-acoustic microscope systems 2000 shown in FIGS. 7 and 25. The processing system 2600 may be a semiconductor wafer processing system, although the use of the exemplary embodiments of this invention are not limited to only systems that process semiconductor wafers. The processing system 2600 can include process controller 2610 that is bidirectionally coupled through a process bus 2615 to the opto-acoustic microscope systems 2000 and to various ones of a plurality of process stations 2620, such as Process Station_1, Process Station_2, . . . , Process Station_n. Individual ones of the process stations 2620 can each perform a different type of processing on a wafer as it progresses through the processing system 2600 in accordance with a process flow. One or more robotic wafer handlers (not shown) can be used to move the wafer through the processing system 2600. Individual ones of the process stations 2620 can perform operations such as, but not limited to, oxidation, metal and/or semiconductor deposition (e.g., chemical vapor deposition (CVD)), ion implantation, photoresist processing, photoresist exposure, photoresist development, etching (chemical and/or non-chemical-based etching), photoresist separation and/or the CMP processing that was discussed above. One or more these processes can be repeated one or more times. At various stages of the processing the wafer will need to be accurately positioned, such as when it is aligned and registered with, for example, a mask. At various stages of the processing the surface features of the wafer need to be examined and/or characterized so as to ensure the quality of a just-completed process. In accordance with this aspect of the invention the one or more opto-acoustic microscope systems 2000 are used to detect, measure and/or characterize surface features of the wafer, and to report the results to the process controller 2610 to assist in its operation. Note that the process controller 2610 can be implemented as one or more data processors, and may include the functionality of the comparator 2020, parameter adjust block 2030, simulator 2010 and library 2015, as shown in FIG. 25.

Note also that the one or more opto-acoustic microscope systems 2000 may be used in conjunction with other types of metrology systems such as, but not limited to, an interferometric-based system such as one described in U.S. Pat. No. 7,193,726 B2, Optical Interferometry, Henry A. Hill.

In other embodiments of this invention the processing system 2600 may be used during the manufacture of liquid crystal displays or plasma displays, as two non-limiting examples.

Discussed now are embodiments for positioning the acousto-optic transducer assembly (AOTA) 10 above an area of interest on a wafer sample 1012.

In order to make a measurement it is typically necessary to move the AOTA 10, or alternatively the sample 1012, so that the region of the AOTA 10 onto which the pump and probe beams are directed is directly above a feature of interest. The lateral linear dimensions of the films making up the AOTA 10 may be as large as, for example, 1000 microns or as small as, for example, 1 micron. The pump and probe beams are typically directed onto only a part of the total area of the AOTA 10, unless the linear dimensions of the AOTA 10 are at the lower end of the range just mentioned. Thus, for example, the AOTA 10 might be a square of side 300 microns, but the area onto which the pump and probe beams are directed may be defined by a circular spot of diameter 10 microns that is positioned somewhere within the total area of the AOTA 10. If the AOTA 10 is composed of layers of unpatterned films, including at least one metal film in which the pump light is absorbed, the AOTA 10 will be substantially opaque. As such, it would be technically challenging to use a microscope to look through the AOTA 10 to determine the position of the AOTA 10 relative to a feature or features of interest on the sample surface 1012A. This will make it difficult to position the pump and probe beams at the correct location on the AOTA 10 in order to make a measurement of a feature of interest.

Figure 27A:
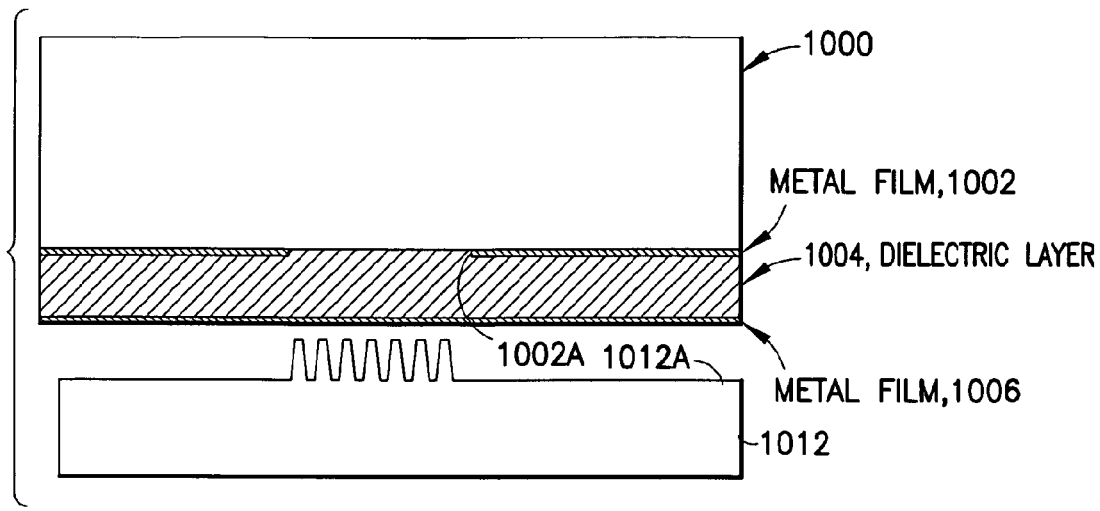
FIGS. 27A, 27B and 27C depict an embodiment wherein at least one aperture is made in at least one film of the acousto-optic transducer assembly to facilitate the positioning thereof relative to a feature or features of interest on a sample surface.
Figure 27B:
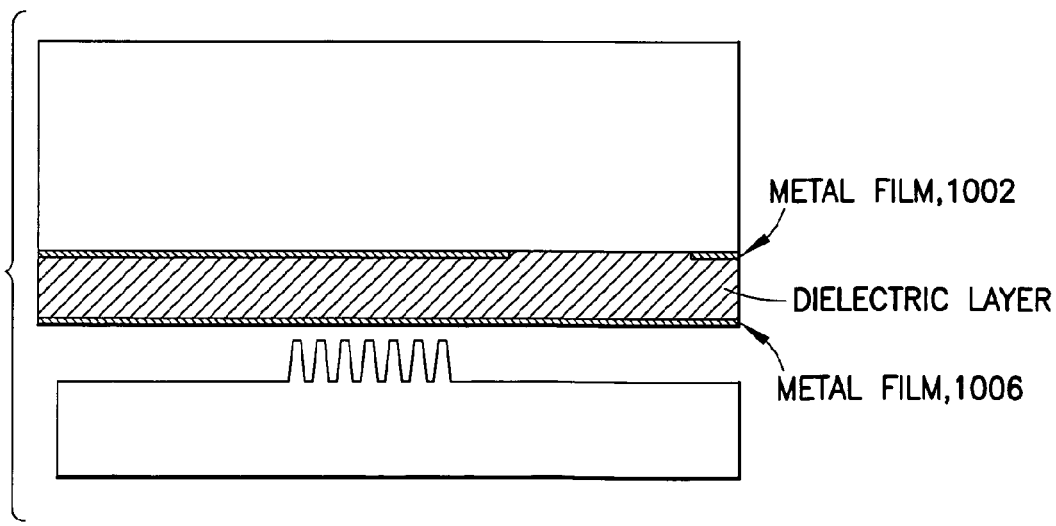
Figure 27C:
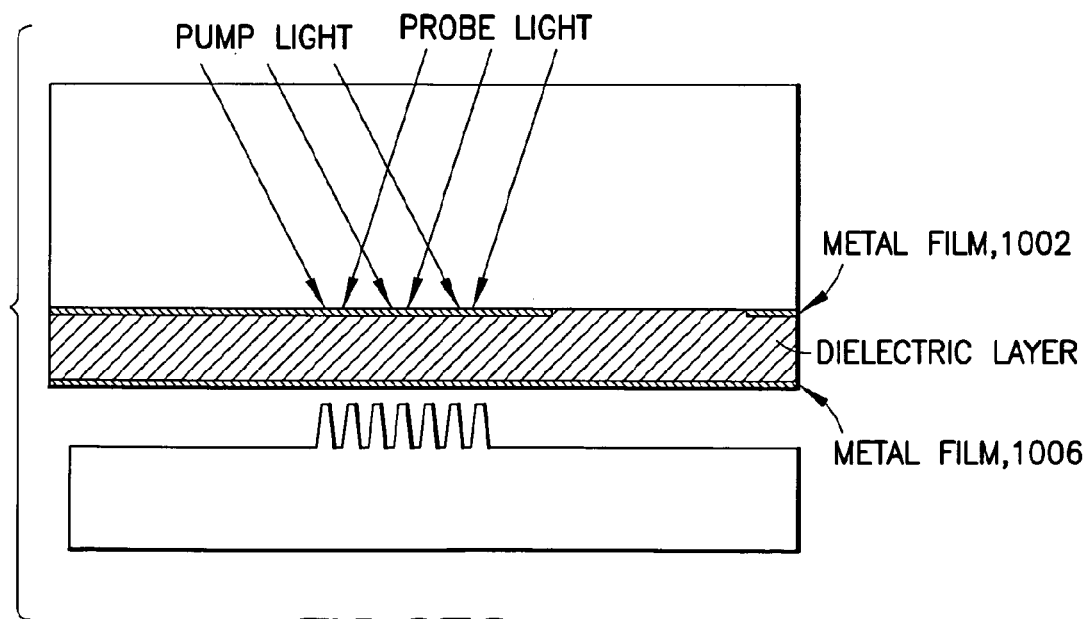

Referring to FIGS. 27A-27C, the positioning of the AOTA 10 is facilitated by patterning the AOTA 10 so as to leave at least one aperture 1002A through which features on the sample surface 1012A, e.g., the wafer surface, can be seen, such as through a microscope (not shown). Thus, for example, it becomes possible to:

1) move the AOTA 10 so that a feature of interest is visible through the aperture 1002A (FIG. 27A);

2) move the AOTA 10 by some predetermined distance so that the aperture is no longer above the feature of interest (FIG. 27B); and 3) in FIG. 27C, direct the pump and robe beams to the location initially occupied by the aperture 1002A in FIG. 27A.

As a variation of this procedure one may:

1) locate a feature (e.g., a reference feature) on the sample surface 1012A other than the feature of interest on which a measurement is to be made, where the position of the feature relative to the feature of interest is assumed to be known in advance; and 2) direct the pump and probe beams to the position on the AOTA 10 that is directly above the feature of interest.

As a further embodiment the AOTA 10 may be fabricated from materials selected such that the pump light is absorbed in one or more films, but the materials selected are such that for some range of light wavelengths light can pass through the AOTA 10. For example, the film in which the pump light is absorbed may be a semiconductor material (as opposed to metal) so that light with photon energy less than the band gap energy of the semiconductor material can pass through this film. In this case a microscope that uses light in this wavelength range can be used to view features on the sample surface 1012A directly.

Based on the foregoing description of the exemplary embodiments, it should be appreciated that these exemplary embodiments also encompass at least one method, and a computer readable medium that stores computer program instructions that, when executed, result in the performance of the at least one method.

Figure 28:
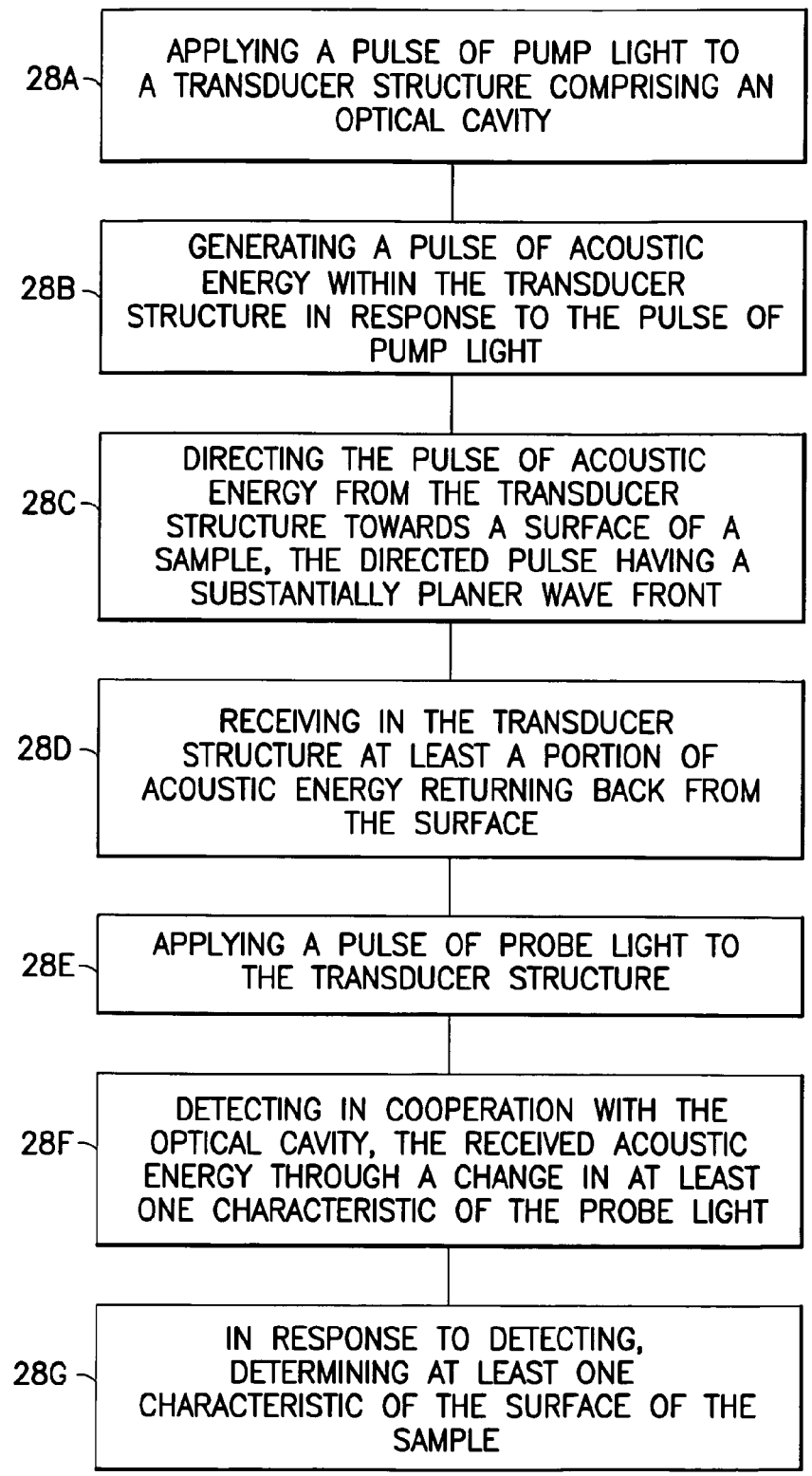
FIG. 28 is a logic flow diagram that is descriptive of a method, and the result of execution of computer program instructions, in accordance with the exemplary embodiments of this invention.

Referring to FIG. 28, the at least one method includes: (Block 28A) applying a pulse of pump light to a transducer structure comprising an optical cavity; (Block 28B) generating a pulse of acoustic energy within the transducer structure in response to the pulse of pump light; (Block 28C) directing the pulse of acoustic energy from the transducer structure towards a surface of a sample, the directed pulse having a substantially planar wave front; (Block 28D) receiving in the transducer structure at least a portion of acoustic energy returning back from the surface; (Block 28E) applying a pulse of probe light to the transducer structure; (Block 28F) detecting, in cooperation with the optical cavity, the received acoustic energy through a change in at least one characteristic of the probe light; and (Block 28G) in response to detecting, determining at least one characteristic of the surface of the sample.

In the foregoing method, the pulse of pump light and the pulse of probe light are obtained from one of first and second laser sources, or from one laser source.

In the foregoing method, the at least one detected characteristic may comprise at least one of intensity, phase, polarization and angle.

In the foregoing method, the determined at least one characteristic may comprise a presence or absence of at least one surface feature, and/or at least one of a height or a depth of at least one surface feature, and an amount of curvature of at least one surface feature, and/or a thickness of at least one film disposed on the surface of the sample.

In the foregoing method, the determined at least one characteristic may indicate a registration between the transducer structure and the surface of the sample.

In the foregoing method, the determined at least one characteristic may be obtained by adjusting input parameters to a simulation to obtain best fit parameters indicative of the at least one characteristic of the sample, and the determined at least one characteristic may be obtained by comparison to a library comprised of results obtained by at least one of simulations and measurements made from at least one reference sample.

The foregoing method may be executed during processing of a semiconductor wafer, and it may be executed, as a non-limiting example, during a polishing process performed on the semiconductor wafer, where the determined at least one characteristic is indicative of at least one of wafer-scale and chip-scale process nonuniformities that may result from performance of the polishing process. Execution of the foregoing method may be used to characterize a surface feature having dimensions less than about 50 nm.

In the foregoing method, there may be a step of viewing a portion of the sample surface through an aperture made through a film that comprises part of the transducer structure; or viewing a portion of the sample surface through a film that comprises part of the transducer structure using wavelengths of light to which the film is at least partially transmissive.

In the foregoing method, there may be a step of tuning the optical cavity. In an exemplary embodiment the optical cavity may comprise an air gap, and tuning may comprise changing a width of the air gap in response to application of an electrical signal.

In the foregoing method, the substantially planar wave front has one of a substantially constant amplitude or a spatially varying amplitude when it impinges on the surface of the sample.

The method may be executed as part of a first measurement method, and determining at least one characteristic of the surface of the sample may be performed in conjunction with a result of a measurement made by at least one second measurement method.

In the foregoing method, the pump and probe light may be delivered to the transducer structure through an optical fiber.

In the foregoing method, the steps of directing and receiving occur through a coupling medium interposed between a surface of the transducer structure and the surface of the sample, and the method may also include a step of varying a temperature of the coupling medium during execution of the method.

The foregoing description has provided by way of exemplary and non-limiting examples a full and informative description of the exemplary embodiments of this invention. However, various modifications and adaptations may become apparent to those skilled in the relevant arts in view of the foregoing description, when read in conjunction with the accompanying drawings and the appended claims. For example, the use of other similar or equivalent wavelengths, materials, dimensions, sample types and the like may be attempted by those skilled in the art. In addition, certain method/process/computational steps and procedures may be performed in other than the order expressly indicated. However, all such and similar modifications of the teachings of this invention will still fall within the scope of the embodiments of this invention.

Furthermore, some of the features of the preferred embodiments of this invention may be used to advantage without the corresponding use of other features. As such, the foregoing description should be considered as merely illustrative of the principles, teachings and embodiments of this invention, and not in limitation thereof.

What is claimed is:

1. An opto-acoustic transducer structure, comprising:
at least one metal or semiconducting film in which a part of a pump light pulse is absorbed to generate a sound wave;
a surface through which the generated sound wave exits the transducer structure and is launched towards a sample, and further through which a sound wave returning from the sample is collected and enters the transducer structure; and
at least one dielectric film;
wherein thicknesses and optical properties of the at least one metal or semiconducting film and the at least one dielectric film are selected so that the returning sound wave results in a measurable change in an optical reflectivity and/or some other optical characteristic of the transducer structure; and
further wherein the sound wave that is launched towards the sample through the surface has a substantially planar wave front.

2. An opto-acoustic transducer assembly comprising:
a substrate having a top surface, for receiving a pump light and a probe light, and a bottom surface; and
a transducer structure coupled to the bottom surface,
said transducer structure comprising an optical cavity and configured to generate sound waves in response to the pump light,
said transducer structure having an output surface configured to direct the generated sound waves towards a sample and to collect sound waves returning from the sample, and
said output surface being shaped so as to provide no significant focusing of the generated sound waves when the sound waves are launched towards a surface of the sample.

3. The transducer assembly of claim 2, wherein said output surface is shaped to direct a substantially planar sound wave towards the sample.

4. The transducer assembly as in claim 2, wherein said transducer structure is comprised of a layer of dielectric material that is interposed between two non-dielectric layers, and wherein a thickness of said layer of dielectric material is selected to have a value that is related to a wavelength of the probe light and is modifiable by the collected sound waves to cause a detectable change in the probe light.

5. The transducer assembly according to claim 2, wherein said transducer structure is comprised of an optical micro-cavity layer that is interposed between a metal-containing layer and a multi-layered dielectric stack, and wherein a thickness of said optical micro-cavity layer is selected to have a value that is related to a wavelength of the probe light and is modifiable by the collected sound waves to cause a detectable change in the probe light.

6. The transducer assembly as in claim 2, wherein the output surface is patterned.

7. The transducer assembly as in claim 2, wherein said output surface is patterned to generate a detection signal that indicates a registration between the transducer assembly and the surface of the sample.

8. The transducer assembly as in claim 2, having an output coupled to means for adjusting input parameters to a simulator based on acoustic signals detected from the sample to obtain best fit parameters indicative of the sample.

9. The transducer assembly as in claim 2, having an output coupled to means for comparing acoustic signals detected from the sample to a library of simulation results, said comparing means indicating a best fit between acoustic signals detected from the sample and at least one simulation result found in the library.

10. The transducer assembly as in claim 2, embodied as a part of an equipment used to process a semiconductor wafer.

11. The transducer assembly as in claim 2, embodied as a part of a system that performs a chemical mechanical polish process on a semiconductor wafer, said transducer assembly operable for detecting at least one of wafer-scale and chip-scale process non-uniformities that may result from the chemical mechanical polish process.

12. The transducer assembly as in claim 2, embodied as a part of an equipment used to process the sample and operable to detect and enable characterization of surface features having dimensions less than about 50 nm.

13. The transducer assembly as in claim 2, wherein said transducer structure includes at least one film in which a part of the pump light is absorbed to generate the sound waves, and further wherein the at least one film has at least one aperture made therein enabling a surface of the sample to be viewed through the transducer structure.

14. The transducer assembly as in claim 2, wherein said transducer structure includes at least one film in which a part of the pump light is absorbed to generate the sound waves, and further wherein the at least one film is comprised of a material that is at least partially transmissive to light of certain wavelengths for enabling the surface of the sample to be viewed, using the certain wavelengths, through the at least one film.

15. The transducer assembly as in claim 2, wherein said optical cavity is bounded by first and second metal-containing films, and futher wherein a metal in the first metal-containing film differs from a metal in the second metal-containing film.

16. The transducer assembly as in claim 2, further comprising means for tuning said optical cavity.

17. The transducer assembly of claim 16, wherein said optical cavity is comprised of one of a whispering gallery resonator and an optical ring resonator.

18. The transducer assembly as in claim 2, wherein said optical cavity comprises an air gap.

19. The transducer assembly as in claim 18, further comprising means for electrostatically changing a width of said air gap.

20. The transducer assembly as in claim 2, wherein multiple pump pulses arriving at different angles are received by said top surface such that the intensity of pump light spatially varies within the transducer assembly resulting in a spatial variation in amplitude of the generated sound waves that are directed towards the sample.

21. The transducer assembly as in claim 2, wherein said transducer assembly forms part of a first measurement system and is configured to generate a first detection signal that is used with a second detection signal generated from the sample by at least one second measurement system.

22. The transducer assembly as in claim 2, wherein said substrate is comprised of diamond.

23. The transducer assembly as in claim 2, coupled to an end of an optical fiber through which the pump light and the probe light are delivered.

24. An opto-acoustic transducer assembly comprising:
a substrate having a top surface, for receiving a pump light and a probe light, and a bottom surface; and
a transducer structure coupled to the bottom surface,
said transducer structure comprising an optical cavity and configured to generate sound waves in response to the pump light,
said transducer structure having an output surface configured to direct the generated sound waves towards a sample and to collect sound waves returning from the sample, and
said output surface being shaped so as to provide no significant focusing of the generated sound waves when the sound waves are launched towards a surface of the sample,
wherein the surface of the sample is characterized by a presence of at least one feature disposed at some vertical distance above or below a surface of at least one other feature,
and further wherein said transducer assembly is configured to generate a detection signal that indicates the vertical distance.

25. The transducer assembly as in claim 24, wherein said at least one feature has a feature surface, wherein said transducer assembly is configured to generate a detection signal that indicates a radius of curvature of the feature surface.

26. A processing system, comprising:
a process controller;
a plurality of process stations implementing a process flow on a structure under direction of the process controller; and
at least one opto-acoustic microscope system coupled to the process controller and operable for determining at least one characteristic of a surface of the structure,
said opto-acoustic microscope comprising a transducer assembly that comprises a substrate having a top surface, for receiving a pump light and a probe light, and a bottom surface; and
a transducer body coupled to the bottom surface,
said transducer body comprising an optical cavity and configured to generate sound waves in response to the pump light,
said transducer body having an output surface configured to direct the generated sound waves towards the surface of the structure and to collect sound waves returning from the surface of the structure, and
said output surface shaped so as to provide no significant focusing of the generated sound waves when the sound waves are launched towards the surface of the structure.

27. The processing system of claim 26, wherein said output surface is shaped to direct a substantially planar sound wave towards the surface of the structure.

28. The processing system as in claim 26, wherein said transducer assembly is comprised of a layer of dielectric material that is interposed between two non-dielectric layers, and further wherein a thickness of said layer of dielectric material is selected to have a value that is related to a wavelength of the probe light and is modifiable by the collected sound waves to cause a detectable change in the probe light.

29. The processing system as in claim 26, wherein said transducer assembly is comprised of an optical micro-cavity layer that is interposed between a metal-containing layer and a multi-layered dielectric stack, and further wherein a thickness of said optical micro-cavity layer is selected to have a value that is related to a wavelength of the probe light and is modifiable by the collected sound waves to cause a detectable change in the probe light.

30. The processing system as in claim 26, wherein the output surface is patterned.

31. The processing system as in claim 26, wherein the surface of the structure is characterized by a presence of at least one feature disposed at some vertical distance above or below a surface of at least one other feature, and further wherein said transducer assembly is configured to generate a detection signal that indicates the vertical distance.

32. The processing system as in claim 26, wherein the surface of the structure is characterized by a presence of at least one feature disposed at some vertical distance above or below a surface of at least one other feature, and further wherein said output surface is patterned to generate a detection signal that indicates a registration between the transducer assembly and the surface of the structure.

33. The processing system as in claim 26, wherein the surface of the structure is characterized by a presence of at least one feature disposed at some vertical distance above or below a surface of at least one other feature, said at least one feature having a feature surface, and further wherein said transducer assembly is configured to generate a detection signal that is indicative of a radius of curvature of the feature surface.

34. The processing system as in claim 26, wherein said process controller is responsive to an output of said opto-acoustic microscope system to adjust at least one input parameter to a simulator based on acoustic signals detected from the surface of the structure to obtain best fit parameters.

35. The processing system as in claim 26, wherein said process controller is responsive to the output of said opto-acoustic microscope system to compare acoustic signals detected from the surface of the structure to a library of simulation results to obtain a best fit between acoustic signals detected from the surface of the structure and at least one simulation result found in the library.

36. The processing system as in claim 26, wherein the structure is comprised of a semiconductor wafer.

37. The processing system as in claim 36, wherein at least one of the process stations performs a chemical mechanical polish process on the surface of a semiconductor wafer, and further wherein said opto-acoustic microscope system is operated to detect at least one of wafer-scale and chip-scale process nonuniformities that may result from the chemical mechanical polish process.

38. The processing system as in claim 36, wherein said opto-acoustic microscope system is operable to detect and enable characterization of wafer surface features having dimensions less than about 50 nm.

39. A method comprising:
applying a pulse of a pump light to an opto-acoustic transducer structure comprising an optical cavity;
generating a pulse of acoustic energy within the transducer structure in response to the pulse of the pump light;
directing the pulse of acoustic energy from the transducer structure towards a surface of a sample, the directed pulse having a substantially planar wave front;
receiving, in the transducer structure, at least a portion of acoustic energy returning back from the surface;
applying a pulse of a probe light to the transducer structure;

detecting, in cooperation with the optical cavity, the received acoustic energy through a change in at least one characteristic of the probe light; and in response to the detecting, determining at least one characteristic of the surface of the sample.

40. The method of claim 39, wherein the pulse of pump light and the pulse of probe light are obtained from one of first and second laser sources or from one laser source.

41. The method of claim 39, wherein the detected at least one characteristic comprises at least one of intensity, phase, polarization and angle.

42. The method as in claim 39, wherein the determined at least one characteristic comprises a presence or an absence of at least one surface feature.

43. The method as in claim 39, wherein the determined at least one characteristic comprises at least one of a height or a depth of at least one surface feature, and an amount of curvature of at least one surface feature.

44. The method as in claim 39, wherein the determined at least one characteristic comprises a thickness of at least one film disposed on the surface of the sample.

45. The method as in claim 39, wherein the determined at least one characteristic indicates a registration between the transducer structure and the surface of the sample.

46. The method as in claim 39, wherein the determined at least one characteristic is obtained by adjusting input parameters to a simulation to obtain best fit parameters indicative of the at least one characteristic of the sample.

47. The method as in claim 39, wherein the determined at least one characteristic is obtained by comparison to a library comprised of results obtained by at least one of simulations and measurements made from at least one reference sample.

48. The method as in claim 39, executed during processing of a semiconductor wafer.

49. The method of claim 48, executed during a polishing process performed on the semiconductor wafer, wherein the determined at least one characteristic is indicative of at least one of wafer-scale and chip-scale process nonuniformities that may result from performance of the polishing process.

50. The method as in claim 39, operable to characterize a surface feature having dimensions less than about 50 nm.

51. The method of claim 50, further comprising viewing a portion of the sample surface through a film that comprises part of the transducer structure using wavelengths of light to which the film is at least partially transmissive.

52. The method as in claim 39, further comprising viewing a portion of the sample surface through an aperture made through a film that comprises part of the transducer structure.

53. The method as in claim 39, further comprising tuning said optical cavity.

54. The method of claim 53, wherein said optical cavity comprises an air gap, and further wherein the tuning comprises changing a width of said air gap in response to application of an electrical signal.

55. The method as in claim 39, wherein the substantially planar wave front has one of a substantially constant amplitude or a spatially varying amplitude when it impinges on the surface of the sample.

56. The method as in claim 39, executed as part of a first measurement method, wherein determining at least one characteristic of the surface of the sample is performed in conjunction with a result of a measurement made by at least one second measurement method.

57. The method as in claim 39, wherein the pump light and the probe light are delivered to the transducer structure through an optical fiber.

58. The method as in claim 39, wherein the directing and the receiving occur through a coupling medium interposed between a surface of the transducer structure and the surface of the sample.

59. The method of claim 58, further comprising varying a temperature of the coupling medium during execution of the method.

60. A computer-readable medium storing computer program instructions, the execution of which results in a performance of the method as in claim 39.

* * * * *

UNITED STATES PATENT AND TRADEMARK OFFICE
CERTIFICATE OF CORRECTION

PATENT NO. : 8,302,480 B2
APPLICATION NO. : 12/449415
DATED : November 6, 2012
INVENTOR(S) : Maris et al.

Page 1 of 1

It is certified that error appears in the above-identified patent and that said Letters Patent is hereby corrected as shown below:

In the Specification

Col. 1, line 4, please insert -- GOVERNMENT GRANT --

Col. 1, line 5, please insert -- This invention was made with government support under DMR0605355 awarded by National Science Foundation. The government has certain rights in the invention. --

Signed and Sealed this
Seventh Day of July, 2015

Michelle K. Lee
*Director of the United States Patent and Trademark Office*